(12) United States Patent
Keil et al.

(10) Patent No.: US 11,203,593 B2
(45) Date of Patent: Dec. 21, 2021

(54) FORMS OF METHYL {4,6-DIAMINO-2-[1(2-FLUOROBENZYL)-1H-PYRAZOLO[3-4-B]PYRIDINO-3-YL] PYRIMIDINO-5-YL}METHYL CARBAMATE

(71) Applicant: Adverio Pharma GmbH, Leverkusen (DE)

(72) Inventors: Birgit Keil, Duesseldorf (DE); Franz-Josef Mais, Duesseldorf (DE); Winfried Joentgen, Cologne (DE); Alfons Grunenberg, Wuppertal (DE)

(73) Assignee: Adverio Pharma GmbH, Leverkusen (DE)

( * ) Notice: Subject to any disclaimer, the term of this patent is extended or adjusted under 35 U.S.C. 154(b) by 0 days.

(21) Appl. No.: 16/848,249

(22) Filed: Apr. 14, 2020

(65) Prior Publication Data

US 2020/0239469 A1 Jul. 30, 2020

Related U.S. Application Data

(63) Continuation of application No. 16/119,671, filed on Aug. 31, 2018, now Pat. No. 10,662,188, which is a continuation of application No. 15/672,921, filed on Aug. 9, 2017, now Pat. No. 10,087,183, which is a continuation of application No. 14/769,334, filed as application No. PCT/EP2014/053096 on Feb. 18, 2014, now abandoned.

(30) Foreign Application Priority Data

Feb. 21, 2013 (CA) .................... CA 2806895
Feb. 21, 2013 (CA) .................... CA 2807859

(51) Int. Cl.
*C07D 471/04* (2006.01)
*A61K 31/519* (2006.01)

(52) U.S. Cl.
CPC .......... *C07D 471/04* (2013.01); *A61K 31/519* (2013.01)

(58) Field of Classification Search
CPC ..................... C07D 471/04; A61P 31/519
See application file for complete search history.

(56) References Cited

U.S. PATENT DOCUMENTS

| | | | |
|---|---|---|---|
| 5,393,761 A | 2/1995 | Perregaard et al. |
| 5,994,378 A | 11/1999 | Matsuo et al. |
| 6,166,027 A | 12/2000 | Straub et al. |
| 6,180,656 B1 | 1/2001 | Furstner et al. |
| 6,362,178 B1 | 3/2002 | Niewohner et al. |
| 6,451,805 B1 | 9/2002 | Straub et al. |
| 6,469,012 B1 | 10/2002 | Ellis et al. |
| 6,693,102 B2 | 2/2004 | Straub et al. |
| 6,743,798 B1 | 6/2004 | Straub et al. |
| 6,784,179 B2 | 8/2004 | Daugan |
| 6,833,364 B1 | 12/2004 | Straub et al. |
| 6,903,089 B1 | 6/2005 | Stasch et al. |
| 6,919,345 B2 | 7/2005 | Stasch et al. |
| 7,091,198 B1 | 8/2006 | Feurer et al. |
| 7,105,523 B2 | 9/2006 | Stasch et al. |
| 7,115,599 B2 | 10/2006 | Stasch et al. |
| 7,135,474 B2 | 11/2006 | Weigand et al. |
| 7,173,037 B2 | 2/2007 | Alonso-Alija et al. |
| 7,226,941 B2 | 6/2007 | Park et al. |
| 7,410,973 B2 | 8/2008 | Feurer et al. |
| 7,427,617 B2 | 9/2008 | Feurer et al. |
| 7,514,463 B2 | 4/2009 | Georg et al. |
| 7,666,867 B2 | 2/2010 | Makriyannis et al. |
| 7,790,761 B2 | 9/2010 | Garthwaite et al. |
| 8,242,272 B2 | 8/2012 | Jimenez et al. |
| 8,309,551 B2 | 11/2012 | Schirok et al. |
| 8,334,291 B2 | 12/2012 | Schirok et al. |
| 8,492,544 B2 | 7/2013 | Mais et al. |
| 8,501,945 B2 | 8/2013 | Mais et al. |
| 8,802,847 B2 | 8/2014 | Fey |
| 8,853,398 B2 | 10/2014 | Mais |
| 8,921,377 B2 | 10/2014 | Follmann et al. |
| 9,090,609 B2 | 7/2015 | Follmann et al. |
| 9,096,592 B2 | 8/2015 | Follmann |
| 9,150,573 B2 | 10/2015 | Fey |
| 9,216,978 B2 | 12/2015 | Follmann |
| 9,365,574 B2 | 6/2016 | Raghavan et al. |
| 9,884,859 B2 | 2/2018 | Liao |
| 10,189,856 B2 | 1/2019 | Hirth-Dietrich |
| 10,351,562 B2 | 7/2019 | Mais |
| 2004/0235863 A1 | 11/2004 | Feurer et al. |
| 2006/0005239 A1 | 1/2006 | Mondri et al. |
| 2006/0167016 A1 | 7/2006 | Feurer et al. |
| 2007/0072924 A1 | 3/2007 | Semple et al. |

(Continued)

FOREIGN PATENT DOCUMENTS

CA 2346698 A1 4/2000
CA 2809911 A1 3/2012

(Continued)

OTHER PUBLICATIONS

Yu et al., "Vasorelaxant Effect of Isoliquiritigenin, A Novel Soluble Guanylate Cyclase Activator, in Rat Aorta," Brit. J. of Pharmacology, 1995, 114: 1587-1594.

Zhao et al., "Effect of Aspirin, Clopidogrel and Dipyridamole on Soluble Markers of Vascular Function in Normal Volunteers and Patients with Prior Ischaemic Stroke," Platelets, Mar. 2006, vol. 17, No. 2, pp. 100-104.

Byrne, S. et al., "Pharmaceutical Solids: A Strategic Approach to Regulatory Considerations," Pharmaceutical Research, 12(7): 945-954, 1995.

(Continued)

*Primary Examiner* — Tracy Vivlemore
*Assistant Examiner* — Ebenezer O Sackey
(74) *Attorney, Agent, or Firm* — Quarles & Brady LLP

(57) ABSTRACT

This present invention relates to forms of methyl {4.6-diamino-2-[1-(2-fluorobenzyl)-1H-pyrazolo[3.4-b]pyridino-3-yl]pyrimidino-5-yl}methylcarbamate comprising its Modification I. Modification II. mono-DMSO solvate. sesqui-DMSO solvate and ¼-ethyl acetate solvate.

22 Claims, 18 Drawing Sheets

(56) References Cited

U.S. PATENT DOCUMENTS

Figure 1:
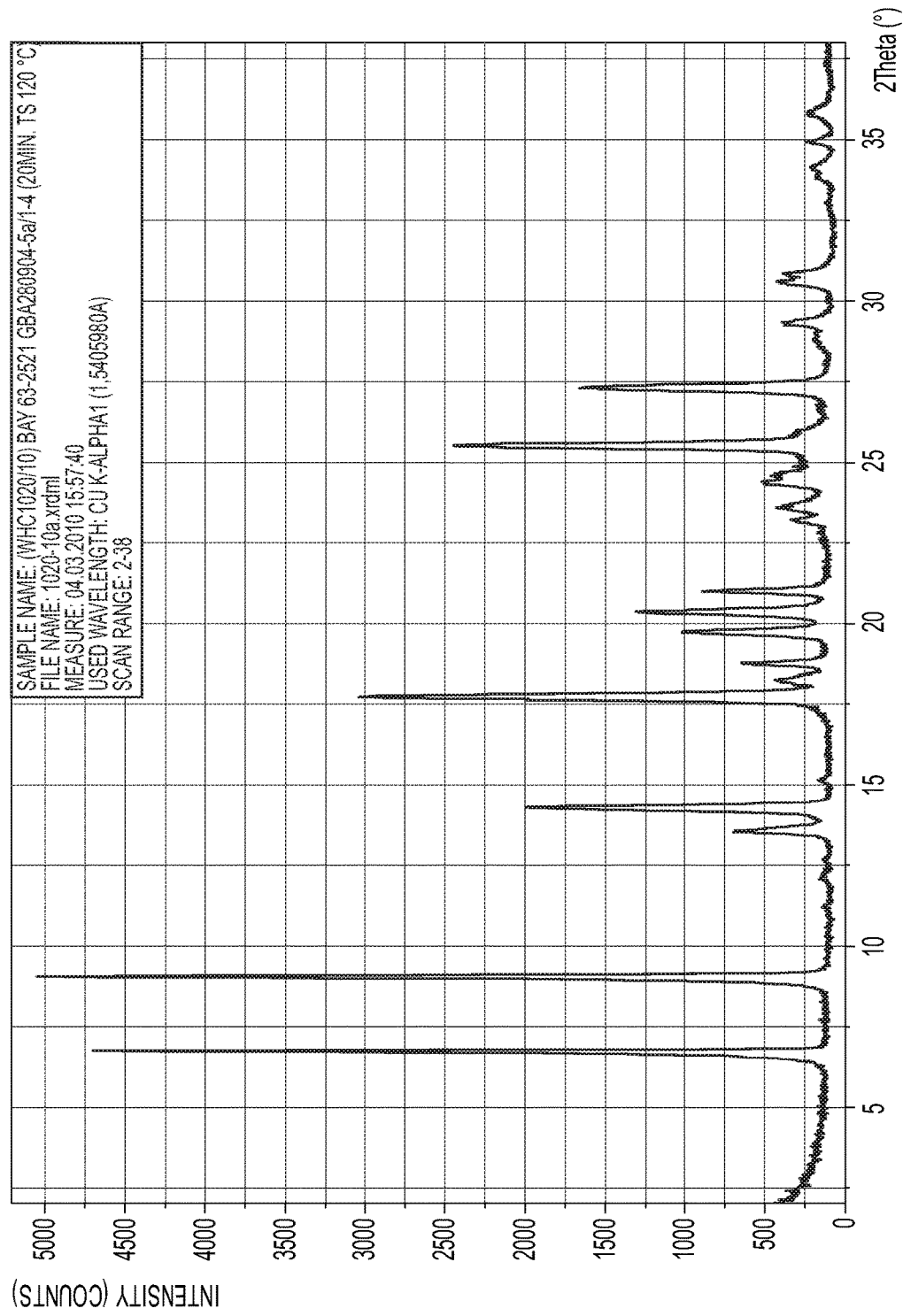

| | | |
|---|---|---|
| 2007/0213332 A1 | 9/2007 | Burkamp et al. |
| 2007/0225299 A1 | 9/2007 | Bischoff et al. |
| 2010/0113507 A1 | 5/2010 | Furstner et al. |
| 2011/0130410 A1 | 6/2011 | Mais et al. |
| 2011/0183928 A1 | 7/2011 | Thede |
| 2011/0183999 A1 | 7/2011 | Grunenberg et al. |
| 2011/0224197 A1 | 9/2011 | Henkel et al. |
| 2012/0022084 A1 | 1/2012 | Follmann et al. |
| 2012/0029002 A1 | 2/2012 | Straub et al. |
| 2012/0149721 A1 | 6/2012 | Stadlwieser |
| 2012/0309724 A1 | 12/2012 | Fleury |
| 2012/0316183 A1 | 12/2012 | Grunenberg et al. |
| 2013/0178475 A1 | 7/2013 | Moore et al. |
| 2013/0210824 A1 | 8/2013 | Follmann |
| 2013/0211090 A1 | 8/2013 | Follmann et al. |
| 2013/0267548 A1 | 10/2013 | Follmann et al. |
| 2013/0310563 A1 | 11/2013 | Mais |
| 2013/0338137 A1 | 12/2013 | Follmann |
| 2014/0288303 A1 | 9/2014 | Mais |
| 2014/0315926 A1 | 10/2014 | Fey |
| 2015/0065533 A1 | 3/2015 | Follmann et al. |
| 2015/0080414 A1 | 3/2015 | Follmann et al. |
| 2016/0009671 A1 | 1/2016 | Fey et al. |
| 2016/0251349 A1 | 9/2016 | Liao |
| 2019/0371469 A1 | 12/2019 | Sandner et al. |

FOREIGN PATENT DOCUMENTS

| | | |
|---|---|---|
| CN | 1613849 A | 5/2005 |
| EP | 0463756 A1 | 1/1992 |
| EP | 0634413 A1 | 1/1995 |
| WO | 0006567 A1 | 2/2000 |
| WO | 03076408 A2 | 9/2003 |
| WO | 03095451 A1 | 11/2003 |
| WO | 2004031187 A1 | 4/2004 |
| WO | 2005046725 A1 | 5/2005 |
| WO | 2009000832 A2 | 12/2008 |
| WO | 2009/064479 A1 | 5/2009 |
| WO | 2009/083739 A1 | 7/2009 |
| WO | 2011064171 A1 | 6/2011 |
| WO | 2011064189 A1 | 6/2011 |
| WO | 2011073118 A1 | 6/2011 |
| WO | 2012028647 A1 | 3/2012 |
| WO | 2017103760 A1 | 6/2017 |

OTHER PUBLICATIONS

Caira, M.R., "Crystalline Polymorphism of Organic Compounds," Topics in Current Chemistry 198: 163-208, 1998.
Written Opinion (PCT/ISR/237) dated Apr. 16, 2014, by the European Patent Office as the International Searching Authority for International Application No. PCT/EP2014/053096.
International Search Report (PCT/ISA/210) dated Apr. 16, 2014, by the European Patent Office as the International Searching Authority for International Application No. PCT/EP2014/053096.
Brittain, H.G., "Polymorphism in Pharmaceutical Solids," 2nd ed., 2009, pp. 1-23; 76-281; 318-346; 436-480; 510-559; 587-629.
Cruz-Cabeza, A.J. et al., 44 Chemical Society Reviews, 8819-8635, 2015.
"Solid State Characterization of Pharmaceuticals," 473-491, 490, (R.A.Storey et al. eds., 2011).
Methner, C. et al., "Riociguant Reduces Infarct Size and Post-Infarct Heart Failure in Mouse Hearts: Insights from MRI/PET Imaging," PLOS One, vol. 8, No. 12, pp. 1-18, 2013.
Stasch, J-P et al., "Soluble Guanylate Cyclase as an Emerging Therapeutic Target in Cardiopulmonary Disease," American Heart Association Circulation, 2263-2273, 2011.
Evgenov, O.V. et al., "NO-independent Stimulators and Activators of Soluble Guanylate Cyclase: Discovery and Therapeutic Potential," Nature Review—Drug Discovery, 755-769, 2011.
Hoeper, M. et al., "Riociguant for Interstitial Lung Disease and Pulmonary Hypertension: a Pilot Trial," 41 European Respiratory Journal, 853-860, 2013.
Grimminger, F. et al., "First Acute Haemodynamic Study of Soluble Guanylate Cyclase Stimular Riociguat in Pulmonary Hypertension," European Respiratory Journal, vol. 33, No. 4, pp. 785-792, 2009.
Cohen, A.T. et al., "Venous Thromboembolism Risk and Prophylaxis in the Acute Hospital Care Setting (ENDORSE Study): a Multinational Cross-Sectional Study," The Lancet, 2008, pp. 387-394.
Schmidt, H.W. et al., "NO- and Haem-Independent Soluble Guanylate Cyclase Activators," 191 Handbook of Experimental Pharmacology, 2009.
Mittendorf, J. et al, "Discovery of Riociguat (BAY 63-2521): A Potent, Oral Stimulator of Soluble Guanylate Cyclase for the Treatment of Pulmonary Hypertension," ChemMedChem, Wiley-VCH Verlag GmbH & Co. KGaA, 2009, vol. 4, pp. 853-865.
Hughey, J.R. et al., "Solid-State Techniques for Improving Solubility in," AAPS Advances in Pharmaceutical Sciences Series, D. Crommelin ed., 2012.
Kratochvil, B, "Solid Forms of Pharmaceutical Molecules," Glassy, Amorphous and Nano-Crystalline Materials, J. Simon ed., 2011.
Van Den Mooter, G., "The Use of Amorphous Solid Dispersions: A Formulation Strategy to Overcome Poor Solubility and Dissolution Rate," 9 Drug Discovery Today: Technologies, e79-e85, 2012.
Morissette, S.L. et al., "High-throughput Crystallization: Polymorphs, Salts, Co-Crystals and Solvates of Pharmaceutical Solids," 56 Advanced Drug Delivery Reviews, 275-300, 276, 2004.
Guillory, J.K., "Generation of Polymorphs, Hydrates, Solvates, and Amorphous Solids," Polymorphism in Pharmaceutical Solids, 183-220, 188, H.G. Brittain ed., 1999.
Barraclough et al., "Mono-Aroylation of 2,3- and 3,4-Diaminopyridine and 4,5-Diaminopyrimidine, and Syntheses of Putative Inotrope/beta-Adrenoceptor Anatagonists," Journal of Chemical Research (M), 1996, vol. 9, pp. 2316-2335.
Becker et al., "NO-independent Regulatory Site of Direct sGC Stimulators like YC-1 and BAY 41-2272," BMC Pharmacology, Dec. 28, 2001, vol. 1, No. 13, pp. 1-12.
Cavalieri et al., "A Synthesis of Adenine: The Incorporation of Isotopes of Nitrogen and Carbon," J. Am. Chem. Soc., Feb. 1949, 71:533-536.
Cheng et al., "Potential Purine Antagonists VII. Synthesis of 6-Alkylpyrazolo-[3,4-d]pyrimidines," The Journal of Organic Chemistry, Feb. 1958, vol. 23, No. 2, pp. 191-200.
Corsi et al.,"1-Halobenzyl-1H-indazole-3-carboxylic acids. A New Class of Antispermatogenic Agents," Journal of Medicinal Chemistry, 1976, vol. 19, No. 6, pp. 778-783.
Evans et al., "The Preparation of 4-Amino- and Other Pteridines," J. of Chem. Soc., 1956, pp. 4106-4113.
Evgenov et al., "NO-independent Stimulators and Activators of Soluble Guanylate Cyclase: Discovery and Therapeutic Potential," Nature Reviews Drug Discovery, Sep. 2006, vol. 5, No. 9, pp. 755-768.
Funabiki et al., "Fluoride Ion-Promoted Reaction of Polyfluoro-1-propenyl p-Toluenesulfonate with Amines. High Efficient and General Access to (Z)-alpha-Fluoro-beta-amino Acrylaldehydes," Chemistry Letters, 1994, vol. 6, pp. 1075-1078.
Ghofrani et al., "Soluble Guanylate Cyclase Stimulation: an Emerging Option in Pulmonary Hypertension Therapy," European Respiratory Review, 2009, vol. 18, No. 11, pp. 35-41.
Glass et al., "Stimulation of Human Platelet Guanylate Cyclase by Fatty Acids," The Journal of Biological Chemistry, Feb. 25, 1977, vol. 252, No. 4, pp. 1279-1285.
Greene et al., "The cGMP Signaling Pathway as a Therapeutic Target in Heart Failure with Preserved Ejection Fraction," Journal of the American Heart Association, Dec. 11, 2013, vol. 2, No. 6, pp. 1-11.
Hajos et al., "Product Class 5: Azaindolizines with Two Nitrogen Atoms in the Five-Membered Ring," Science of Synthesis, 2002, vol. 12, pp. 613-678.
Hassan et al., "Aryl-Aryl Bond Formation One Century after the Discovery of the Ullmann Reaction," Chemical Reviews, Mar. 8, 2002, vol. 102, No. 5, pp. 1359-1470.
Hughes, "Progress in the Mitsunobus Reaction: a Review," Organic Preparations and Procedures Int., 1996, vol. 28, No. 2, pp. 127-164.

(56) References Cited

OTHER PUBLICATIONS

Kim et al., "Cirsium Japonicum Elicits Endothelium-Dependent Relaxation via Histamine H1-receptor in Rat Thoracic Aorta," Journal of Ethnopharmacology, 2008, vol. 116, pp. 223-227.

Ko et al., "YC-1, a Novel Activator of Platelet Guanylate Cyclase," Blood, Dec. 15, 1994, vol. 84, No. 12, pp. 4226-4233.

Li et al., "Synthesis and Structure-Activity Relationships of 2-Pyridones: A Novel Series of Potent DNA Gyrase Inhibitors as Antibacterial Agents," J. Med. Chem., 1996, 39: 3070-3088.

Markovski et al., "Reactions of Pentakis{2,2,3,3-Tetrafluoropropoxy} Phosphorane with Secondary Amines," Zhurnal Obshchei Khimii 1980, 50(4): 826-834.

Mulsch et al., "Effect of YC-1, an NO-independent, Superoxide-sensitive Stimulator of Soluble Guanylyl Cyclase, on Smooth Muscle Responsiveness to Nitrovasodilators," Brit. J. Pharm., 1997, 120: 681-689.

Palacios et al, "A New and Efficient Synthesis of Imidazo[1,5-a] pyridine Derivatives by a Tandem Aza-Wittig/Electrocyclic Ring Closure of N-vinylic Phosphazenes," Tetrahedron, Mar. 20, 1995, vol. 51, No. 12, pp. 3683-3690.

Pettibone et al., "A Structurally Novel Stimulator of Guanylate Cyclase with Long-Lasting Hypotensive Activity in the Dog," European Journal of Pharmacology, Oct. 22, 1985, vol. 116, No. 3, pp. 307-312.

Powers-Martin et al., "Immunohistochemical Assessment of Cyclic Guanosine Monophosphate (cGMP) and Soluble Guanylate Cyclase (sGC) within the Rostral Ventrolateral Medulla," Journal of Biomedical Science, 2008, vol. 15, No. 6, pp. 801-812.

Reichardt et al., "Darstellung von Fluor- und Jodmalondialdehyd," Liebigs Ann. Chem., 1970, 737, pp. 99-107.

Schwoch et al., "189. 2-3-Dihydrospirol [1 H-4 and 5-azabenzimidazole-2,1'-cyclohexane](=Spiro[cyclohexane-1 ,2'(3'H)-1'H-imidazo[4,5-hb]pyridine] and Spiro[cyclohexane-1 ,2(3'H)-1 H-imidazo[4,5-c[pyridine]) Reactions with Nucleophiles," Helvetia Chimica Acta, 1994, 77: 2175-2190.

Sharkovska et al., "Nitric Oxide-independent Stimulation of Soluble Guanylate Cyclase Reduces Organ Damage in Experimental Low-Renin and High-Renin Models," Journal of Hypertension, Aug. 2010, vol. 28, No. 8, pp. 1666-1675.

Stasch et al., "Soluble Guanylate Cyclase as an Emerging Therapeutic Target in Cardiopulmonary Disease," Circulation, May 2011, 123: 2263-2273.

Vippagunta et al., "Crystalline Solids," Advanced Drug Delivery Reviews, 2001, vol. 48, pp. 3-26.

Winn et al., "2-(Alkylamino)nicotinic Acid and Analogs. Potent Angiotensin II Antagonists," J. Med. Chem., 1993, 36: 2676-2688.

Wu et al., "YC-1 Inhibited Human Platelet Aggregation Through NO-Independent Activation of Soluble Guanylate Cyclase," British Journal of Pharmacology, Oct. 1995, vol. 116, No. 3, pp. 1973-1978.

Wunder et al., "A Cell-Based cGMP Assay Useful for Ultra-High-Throughput Screening and Identification of Modulators of the Nitric Oxide/cGMP Pathway," Analytical Biochemistry, Apr. 1, 2005, vol. 339, No. 1, pp. 104-112.

Yamanaka et al., "A New Facile and Efficient Method for the Preparation of (Z)-a-Fiuoro-~-(dialkylamino) Acrylaldehydes from (Polyftuoro-1-propenyl)trimethylammonium Iodide," Synlett, May 1993, 353-354.

Yamanaka et al., "Reactions of Polyfluoroalkyl o-Nitrobenzenesulfonates with Tertiary Amines," Nippon Kagaku Kaishi, 1985, 10: 1988-1994 (in JP+abstract).

Yamanaka et al., "Synthesis and Reactions of (1 H, 1 H, aH-Perfluoroalkyl)-trimethylammonium Halides," Nippon Kagaku Kaishi, 1985, 7:1036-1043 (in JP+abstract).

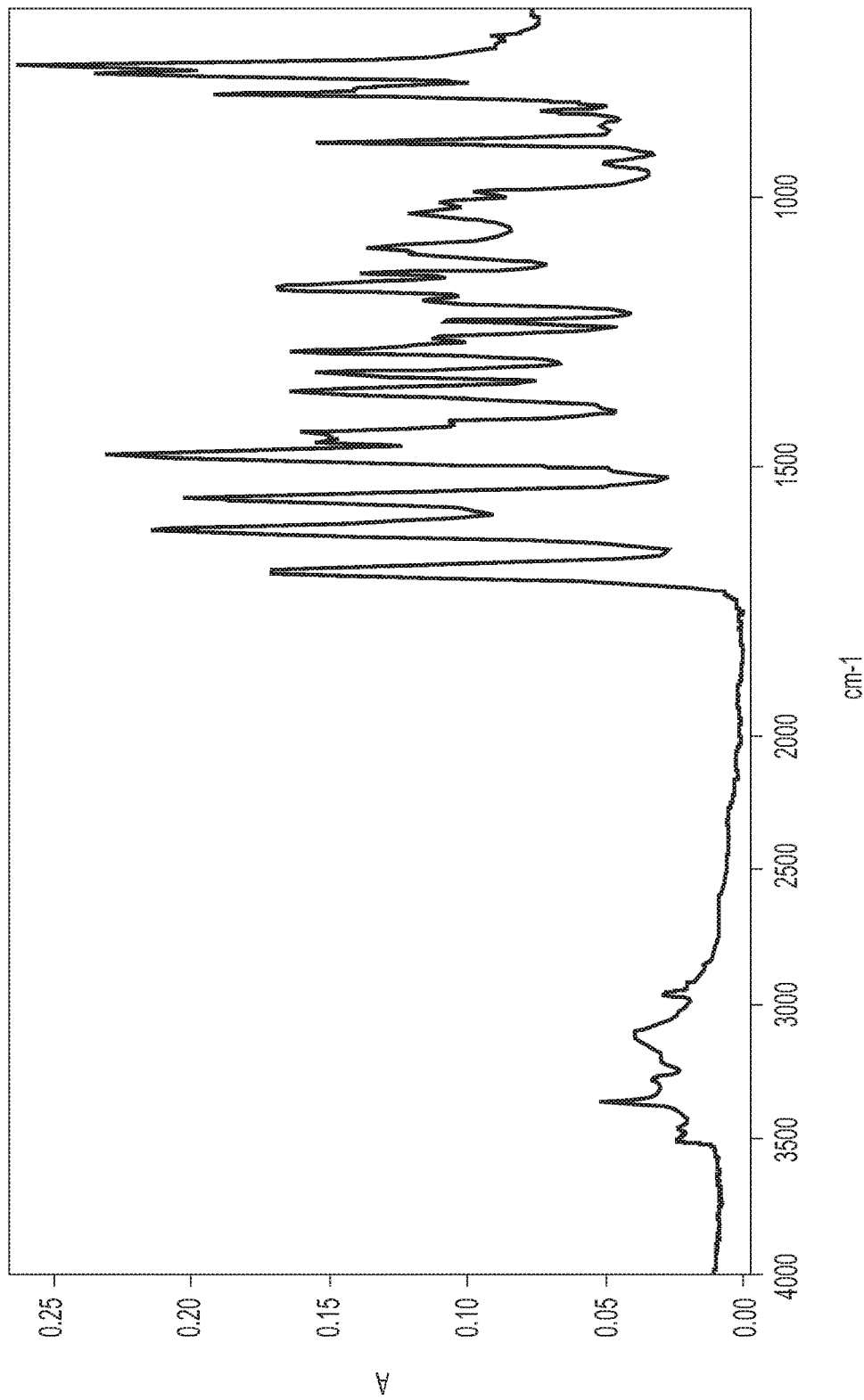

FORMS OF METHYL {4,6-DIAMINO-2-[1(2-FLUOROBENZYL)-1H-PYRAZOLO[3-4-B]PYRIDINO-3-YL] PYRIMIDINO-5-YL}METHYL CARBAMATE

CROSS REFERENCE TO RELATED APPLICATIONS

This application is a continuation of U.S. application Ser. No. 16/119,671, filed Aug. 31, 2018, which is a continuation of U.S. application Ser. No. 15/672,921, filed Aug. 9, 2017, now U.S. Pat. No. 10,087,183, which is a continuation of application Ser. No. 14/769,334, filed Aug. 20, 2015 (abandoned), which is a U.S. national stage entry under 35 U.S.C. 371 of PCT/EP2014/053096, filed Feb. 18, 2014, which claims benefit of priority to Canadian Patent Application Nos. 2,806,895, filed Feb. 21, 2013, and 2,807,859, filed Feb. 21, 2013.

This present invention relates to forms of methyl {4,6-diamino-2-[1-(2-fluorobenzyl)-1H-pyrazolo[3,4-b]pyridino-3-yl]pyrimidino-5-yl}methylcarbamate of formula (I):

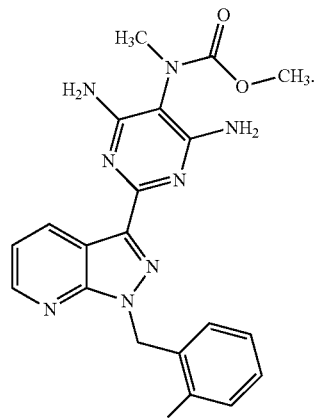

(I)

WO 03/095451 discloses the compound of formula (I), and further describes that this and other compounds disclosed therein are stimulators of soluble guanylate cyclase, and may therefore be used as agents for the prophylaxis and/or treatment of cardiovascular disorders.

WO 03/095451 describes the preparation of the compound of formula (I). However, there are a number of disadvantages associated with the process disclosed in WO 03/095451, as discussed in WO 2011/064171. WO 2011/064171 thus discloses an alternative process for preparing a compound of the formula (I).

In the process of WO 2011/064171, a compound of the formula (VI) is provided:

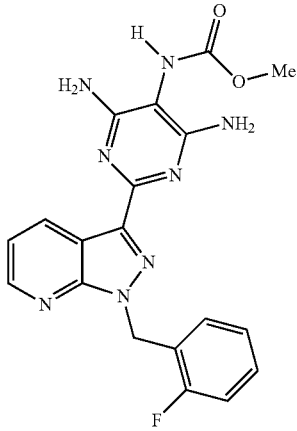

(VI)

The compound of the formula (VI) is reacted in a manner known per se, for example in accordance with one of the descriptions in WO 03/0945451 or ChemMedChem 2009, 4, 853-865, with a methylating agent Me-X to give a crude product which contains high amounts of the compound of the formula (I).

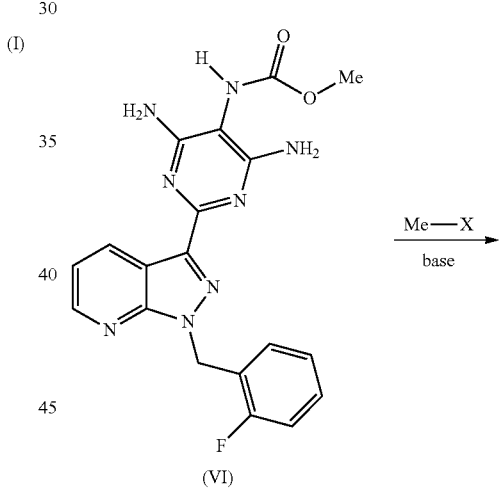

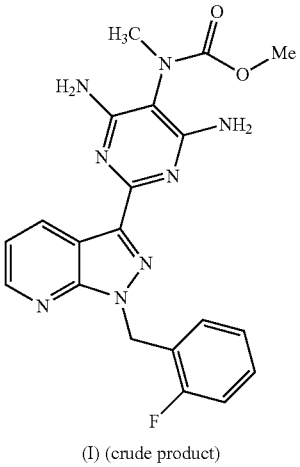

(I) (crude product)

The methylating agent Me-X used is methyl iodide, dimethyl sulphate, methyl toluenesulphonate, etc., and methyl iodide or dimethyl sulphate is preferred.

The purification of the crude product of the formula (I) for use as pharmaceutically active compound is carried out via the compound methyl {4,6-diamino-2-[1-(2-fluorobenzyl)-1H-pyrazolo[3,4-b]pyridin-3-yl]pyrimidin-5-yl}methylcarbamate sulphinyldimethane (1:1), i.e. a compound of the formula (II) as isolated intermediate or generated in a mixture.

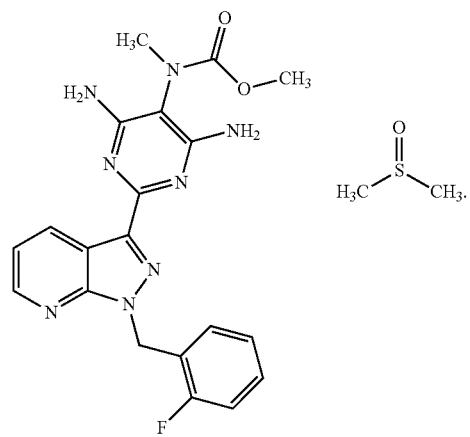

(II)

For the purification, initially, a mixture is formed which contains high amounts of the compound of the formula (II) as intermediate.

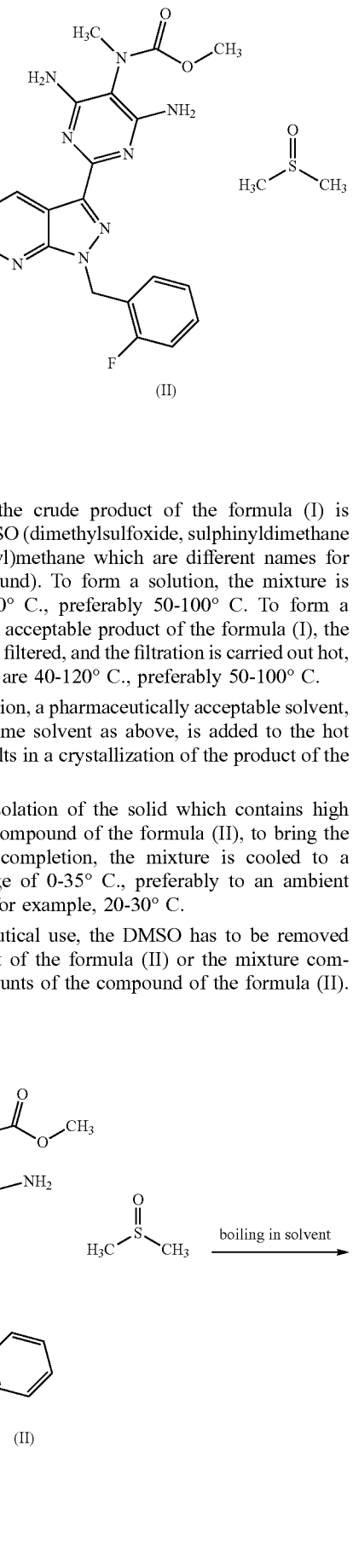

(II)

To this end, the crude product of the formula (I) is dissolved in DMSO (dimethylsulfoxide, sulphinyldimethane or (methylsulfinyl)methane which are different names for the same compound). To form a solution, the mixture is heated to 40-120° C., preferably 50-100° C. To form a pharmaceutically acceptable product of the formula (I), the solution has to be filtered, and the filtration is carried out hot, the temperatures are 40-120° C., preferably 50-100° C.

After the filtration, a pharmaceutically acceptable solvent, preferably the same solvent as above, is added to the hot filtrate. This results in a crystallization of the product of the formula (II).

Prior to the isolation of the solid which contains high amounts of the compound of the formula (II), to bring the precipitation to completion, the mixture is cooled to a temperature range of 0-35° C., preferably to an ambient temperature of, for example, 20-30° C.

For pharmaceutical use, the DMSO has to be removed from the product of the formula (II) or the mixture comprising high amounts of the compound of the formula (II).

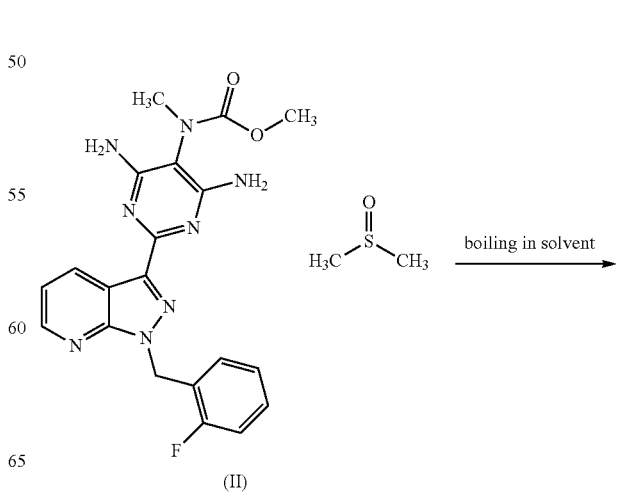

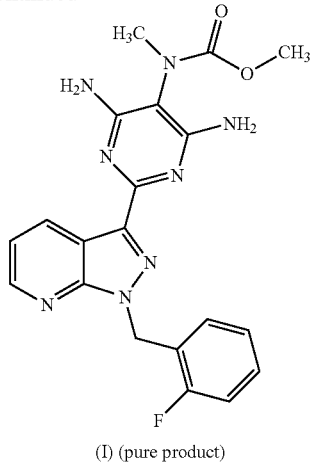

(I) (pure product)

To this end, the product of the formula (II) or the isolated mixture comprising high amounts of the product of the formula (II) is boiled in a pharmaceutically acceptable solvent from the class of the ketones, ethers, esters or alcohols. Examples of such solvents which may be mentioned are: methanol, ethanol, isopropanol, 1-butanol, 2-butanol, ethyl acetate, isopropyl acetate or propyl acetate, butyl acetate, tert-butyl methyl ether, diisopropyl ether, acetone, methyl ethyl ketone, methyl isobutyl ketone, etc. Preference is given to ethanol, isopropanol, ethyl acetate, isopropyl acetate, butyl acetate, methyl ethyl ketone, methyl isobutyl ketone. It is also possible to use mixtures of these solvents. Particular preference is given to ethyl acetate or a mixture of ethyl acetate with ethanol.

Boiling takes place at reflux of the solvent in question or, if appropriate, at slightly elevated pressure. The temperature is 50-150° C., preferably 80-120° C. The solid obtained is then filtered.

The present invention relates to new forms of methyl {4,6-diamino-2-[1-(2-fluorobenzyl)-1H-pyrazolo[3,4-b]pyridino-3-yl]pyrimidino-5-yl}methylcarbamate of formula (I).

Surprisingly it has been found that the compound of formula (I) crystallizes in two modifications with melting points at 268° C. (Modification I) and 250° C. (Modification II). In this context modifications and polymorphs have the same meaning. In addition, three pseudo-polymorphs, a mono-DMSO solvate, a sesqui-DMSO solvate, a ¼-ethyl acetate solvate and the amorphous form have been found. The amorphous form can exist at room temperature, but crystallizes very quickly. All together—modifications or polymorphs, pseudo-polymorphs and amorphous forms—are different forms of the compound of formula (I) according to the present invention.

Aspects of some embodiments of the present invention which may be beneficial in the present pharmaceutical field may include stability (e.g. pressure stability, chemical stability, storage stability), compatibility over other ingredients, purity, solubility (thermodynamically, kinetically), crystallization properties, properties regarding isolation during the chemical synthesis and bioavailability of the forms of the compound of formula (I).

The compound of the formula (I) in the Modification I is the thermodynamically stable form between 0° C. and 80° C.

Two of the solvates occur during synthesis, the mono-DMSO solvate and the ¼-ethyl acetate solvate of the compound of the formula (I). The compound of the formula (I) in the Modification II can form from the solvates after solvent release, e.g. during drying at 80° C.

Embodiments of the present invention are not only each single form the compound of the formula (I) which are Modification I, Modification II, mono-DMSO solvate, sesqui-DMSO solvate and ¼-ethyl acetate solvate of the compound of the formula (I) but also mixtures comprising two, three, four or five forms of the aforementioned.

A pharmaceutical composition according to the present invention comprises preferably only one of the forms selected from the group comprising Modification I, Modification II, mono-DMSO solvate, sesqui-DMSO solvate and ¼-ethyl acetate solvate of the compound of the formula (I) mainly and no significant fractions of another form of the compound of the formula (I), for example of another modification or pseudopolymorph of the compound of the formula (I). More preferably the pharmaceutical composition contains more than 85 percent by weight, more preferably more than 90 percent by weight, most preferably more than 90 percent by weight, and up to 100 percent, of the compound of the formula (I) in one of the aforementioned forms related to the total amount of all forms of the compound of the formula (I) present in the composition.

Preference is given to a pharmaceutical composition comprising the compound of the formula (I) in the Modification I mainly and no significant fractions of another form of the compound of the formula (I), for example of another modification or pseudopolymorph of the compound of the formula (I). The pharmaceutical composition preferably contains more than 85 percent by weight, more preferably more than 90 percent by weight, more preferably more than 95 percent by weight, and up to 100 percent of the compound of the formula (I) in the Modification I related to the total amount of all forms of the compound of the formula (I) present in the composition.

Further preference is given to a pharmaceutical composition comprising the compound of the formula (I) in the Modification II mainly and no significant fractions of another form of the compound of the formula (I), for example of another modification or pseudopolymorph of the compound of the formula (I). The pharmaceutical composition preferably contains more than 85 percent by weight, more preferably more than 90 percent by weight, more preferably more than 95 percent by weight, and up to 100 percent of the compound of the formula (I) in the Modification II related to the total amount of all forms of the compound of the formula (I) present in the composition.

Further preference is given to a pharmaceutical composition comprising the mono-DMSO solvate of the compound of the formula (I) mainly and no significant fractions of another form of the compound of the formula (I), for example of another modification or pseudopolymorph of the compound of the formula (I). The pharmaceutical composition preferably contains more than 85 percent by weight, more preferably more than 90 percent by weight, more preferably more than 95 percent by weight, and up to 100 percent of the mono-DMSO solvate of the compound of the formula (I) related to the total amount of all forms of the compound of the formula (I) present in the composition.

Further preference is given to a pharmaceutical composition comprising the sesqui-DMSO solvate of the compound of the formula (I) mainly and no significant fractions of another form of the compound of the formula (I), for example of another modification or pseudopolymorph of the compound of the formula (I). The pharmaceutical composition preferably contains more than 85 percent by weight, more preferably more than 90 percent by weight, more preferably more than 95 percent by weight, and up to 100 percent of the sesqui-DMSO solvate of the compound of the formula (I) related to the total amount of all forms of the compound of the formula (I) present in the composition.

Further preference is given to a pharmaceutical composition comprising the ¼-ethyl acetate solvate of the compound of the formula (I) mainly and no significant fractions of another form of the compound of the formula (I), for example of another modification or pseudopolymorph of the compound of the formula (I). The pharmaceutical composition preferably contains more than 85 percent by weight, more preferably more than 90 percent by weight, more preferably more than 95 percent by weight, and up to 100 percent of the ¼-ethyl acetate solvate of the compound of the formula (I) related to the total amount of all forms of the compound of the formula (I) present in the composition.

Further preference is given to a pharmaceutical composition comprising only Modification I of the compound of the formula (I) and 0.1 to 10 percent ¼-ethyl acetate solvate of the compound of the formula (I) and no significant fractions of another form of the compound of the formula (I).

Further preference is given to a pharmaceutical composition comprising only Modification I of the compound of the formula (I) and 2.5 to 7.5 percent ¼-ethyl acetate solvate of the compound of the formula (I) and no significant fractions of another form of the compound of the formula (I).

Further preference is given to a pharmaceutical composition comprising only Modification I of the compound of the formula (I) and 5 percent ¼-ethyl acetate solvate of the compound of the formula (I) and no significant fractions of another form of the compound of the formula (I).

Further preference is given to a pharmaceutical composition comprising only Modification I of the compound of the formula (I) and 0.1 to 10 percent mono-DMSO solvate of the compound of the formula (I) and no significant fractions of another form of the compound of the formula (I).

Further preference is given to a pharmaceutical composition comprising only Modification I of the compound of the formula (I) and 1.0 to 5 percent mono-DMSO solvate of the compound of the formula (I) and no significant fractions of another form of the compound of the formula (I).

Further preference is given to a pharmaceutical composition comprising only Modification I of the compound of the formula (I) and 2.5 percent mono-DMSO solvate of the compound of the formula (I) and no significant fractions of another form of the compound of the formula (I).

Further preference is given to a pharmaceutical composition comprising only Modification I of the compound of the formula (I) and 0.1 to 10 percent ¼-ethyl acetate solvate of the compound of the formula (I) and 0.1 to 10 percent mono-DMSO solvate of the compound of the formula (I) and optionally no other form of the compound of the formula (I).

Further preference is given to a pharmaceutical composition comprising only Modification I of the compound of the formula (I) and 2.5 to 7.5 percent ¼-ethyl acetate solvate of the compound of the formula (I) and 1.0 to 5 percent mono-DMSO solvate of the compound of the formula (I) and optionally no other form of the compound of the formula (I).

Further preference is given to a pharmaceutical composition comprising only Modification I of the compound of the formula (I) and 5 percent ¼-ethyl acetate solvate of the compound of the formula (I) and 2.5 percent mono-DMSO solvate of the compound of the formula (I) and optionally no other form of the compound of the formula (I).

Further preference is given to a pharmaceutical composition comprising only Modification I of the compound of the formula (I) and 5 percent ¼-ethyl acetate solvate of the compound of the formula (I) and 2.5 percent mono-DMSO solvate of the compound of the formula (I) and optionally and no significant fractions of another form of the formula (I).

The forms of the compound of the formula (I) of the present invention are used alone or together as a mixture in high purity in pharmaceutical formulations. As mixtures a combination of the compound of formula (I) in the Modification I and the compound of formula (I) in the Modification II, a combination of the compound of formula (I) in the Modification I and the mono-DMSO solvate of the compound of formula (I), a combination of the compound of formula (I) in the Modification I and the sesqui-DMSO solvate of the compound of formula (I), a combination of the compound of formula (I) in the Modification I and the ¼-ethyl acetate solvate of the compound of formula (I), a combination of the compound of formula (I) in the Modification I and the mono-DMSO solvate of the compound of formula (I) and the ¼-ethyl acetate solvate of the compound of formula (I), or a combination of the compound of formula (I) in the Modification I and the sesqui-DMSO solvate of the compound of formula (I) and the ¼-ethyl acetate solvate of the compound of formula (I) optionally with no other form of the compound of the formula (I) are preferred.

The term 'significant fraction' shall have the meaning of no more than 10 percent by weight of the mentioned solvate or Modification of compound of formula (I) and preferably no more than 5 percent.

The different forms of the compound of formula (I) can be distinguished by X-ray powder diffraction, differential scanning calorimetry (DSC), IR-, Raman-, NIR-, FIR- and 13C-solid-state-NMR-spectroscopy:

FIG. 1: X-Ray powder diffractogram of the modification I

Figure 2:
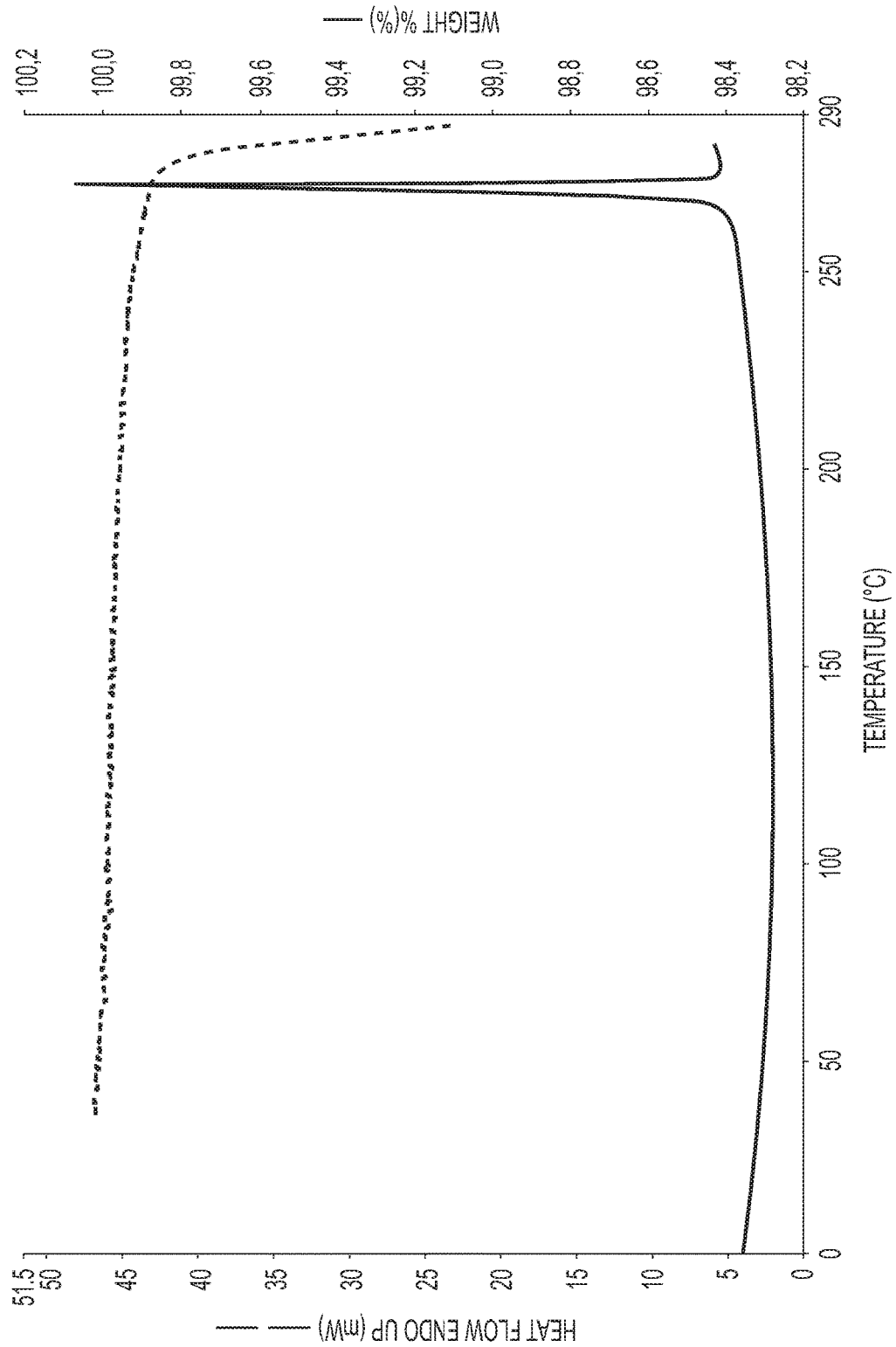

FIG. 2: DSC- and TGA-Thermogram of modification I

Figure 3:
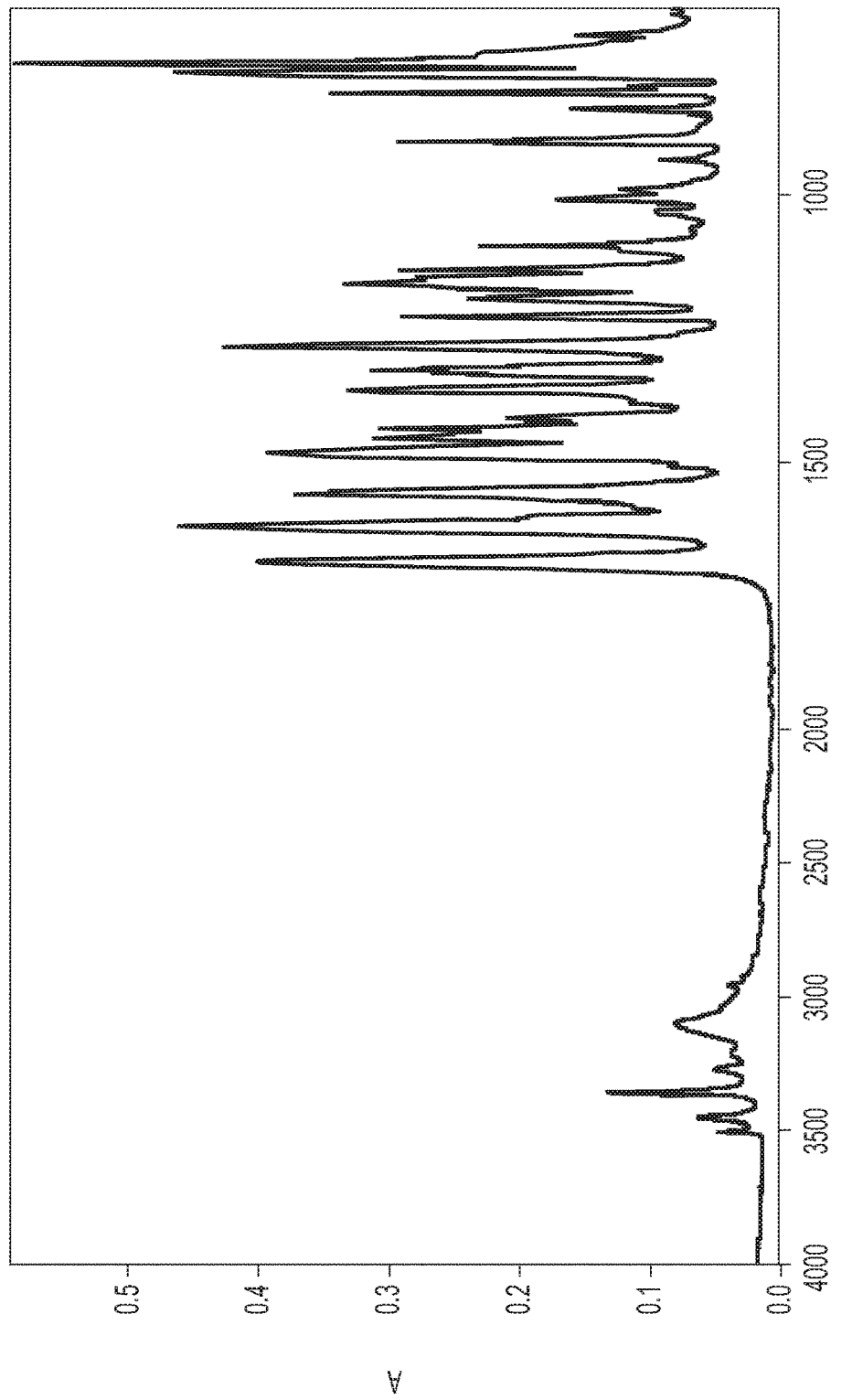

FIG. 3: IR-Spectrum (ATR) of modification I

Figure 4:
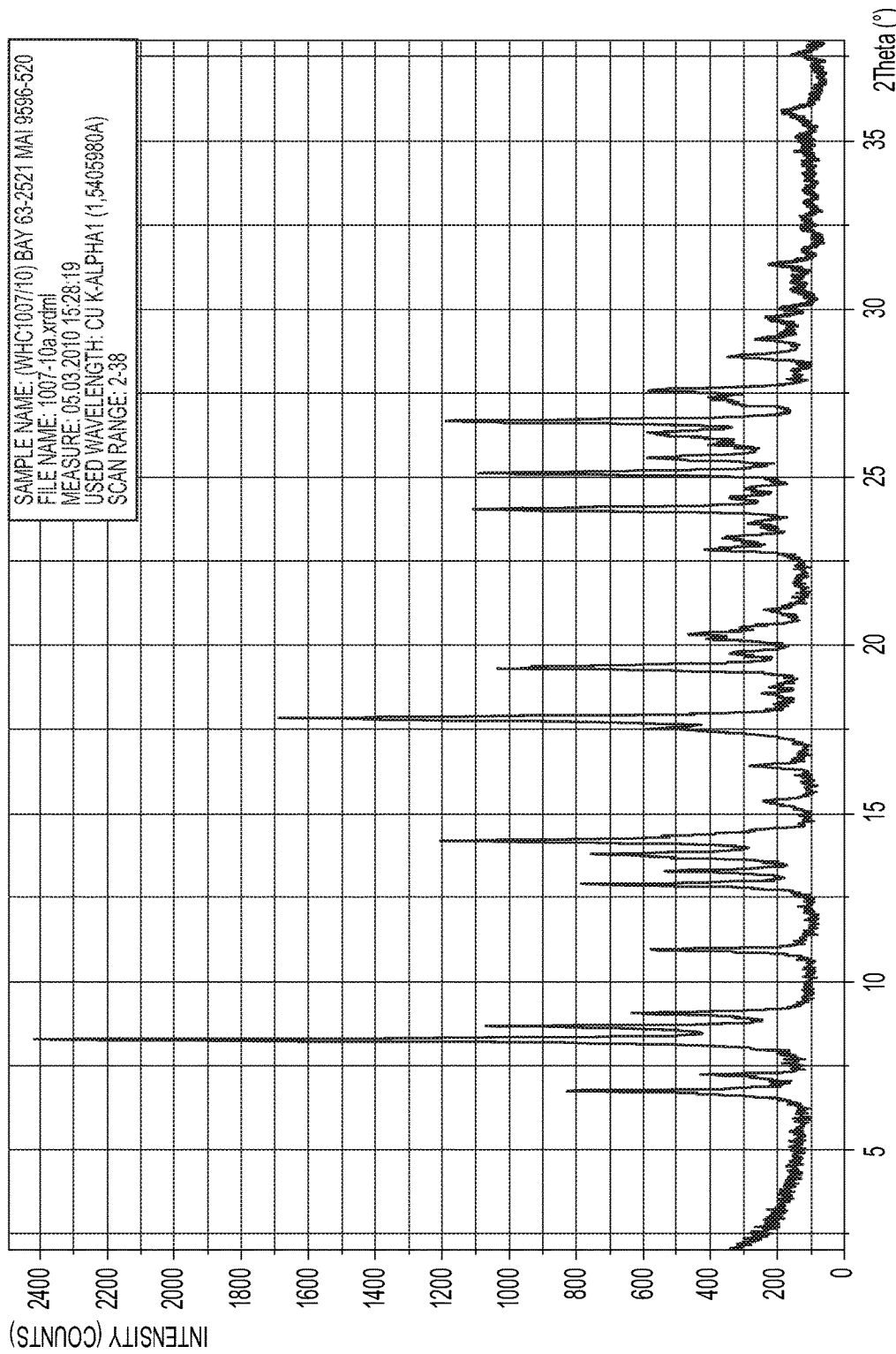

FIG. 4: X-Ray powder diffractogram of the ¼-ethyl acetate solvate

Figure 5:

FIG. 5: DSC- and TGA-Thermogram of the ¼-ethyl acetate solvate

Figure 6:
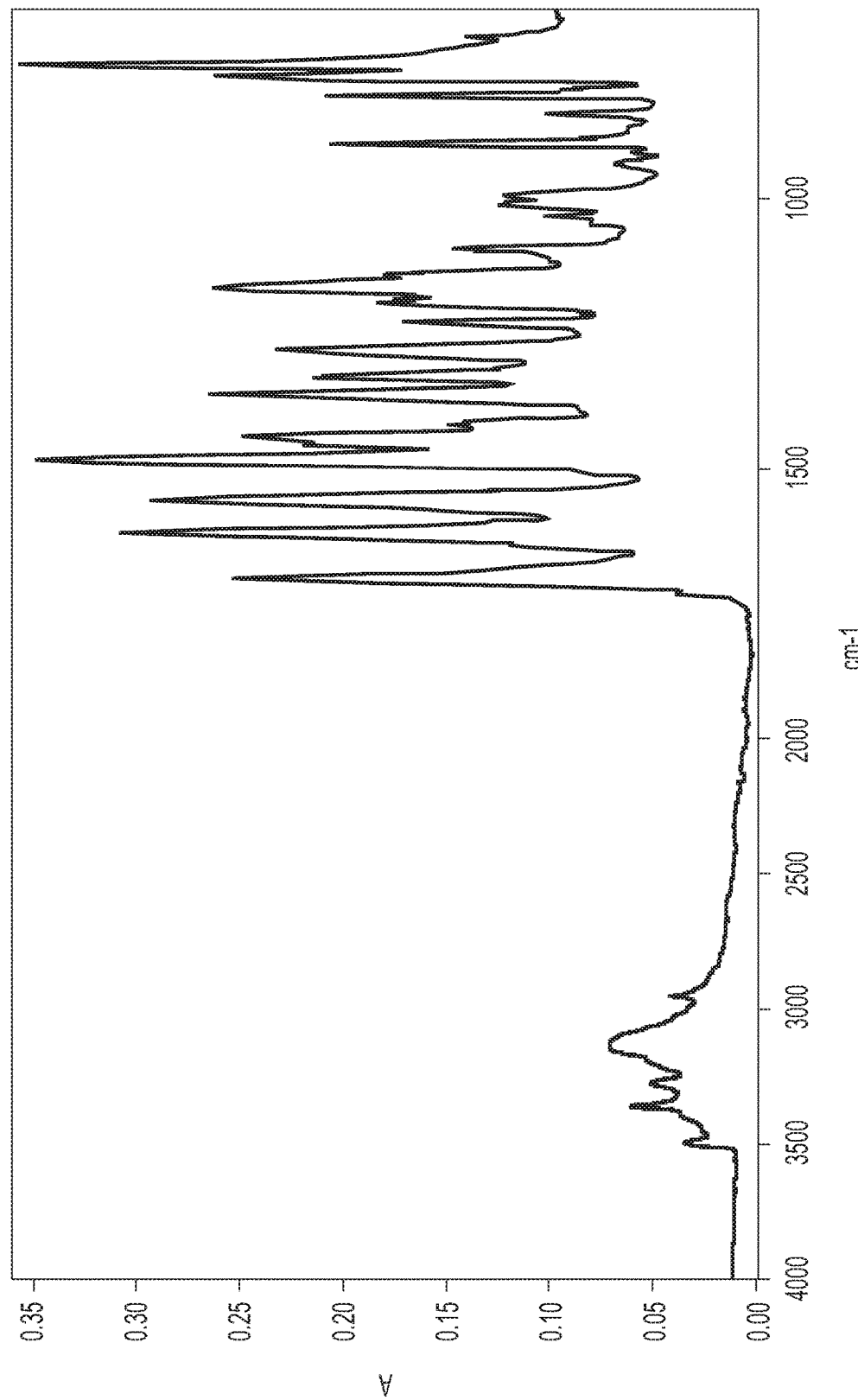

FIG. 6: IR-Spectrum (ATR) of the ¼-ethyl acetate solvate

Figure 7:
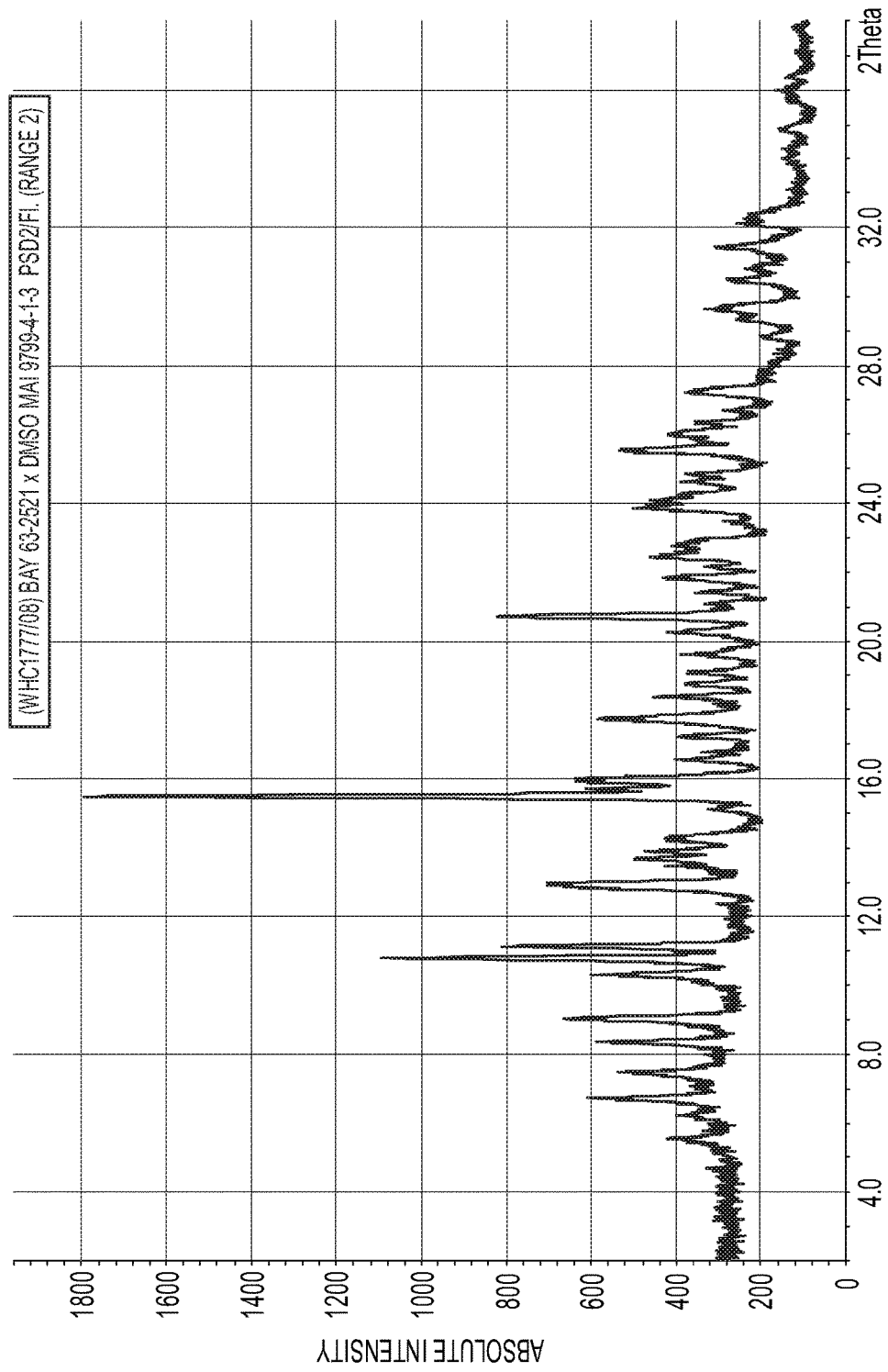

FIG. 7: X-Ray powder diffractogram of the mono-DMSO solvate

Figure 8:
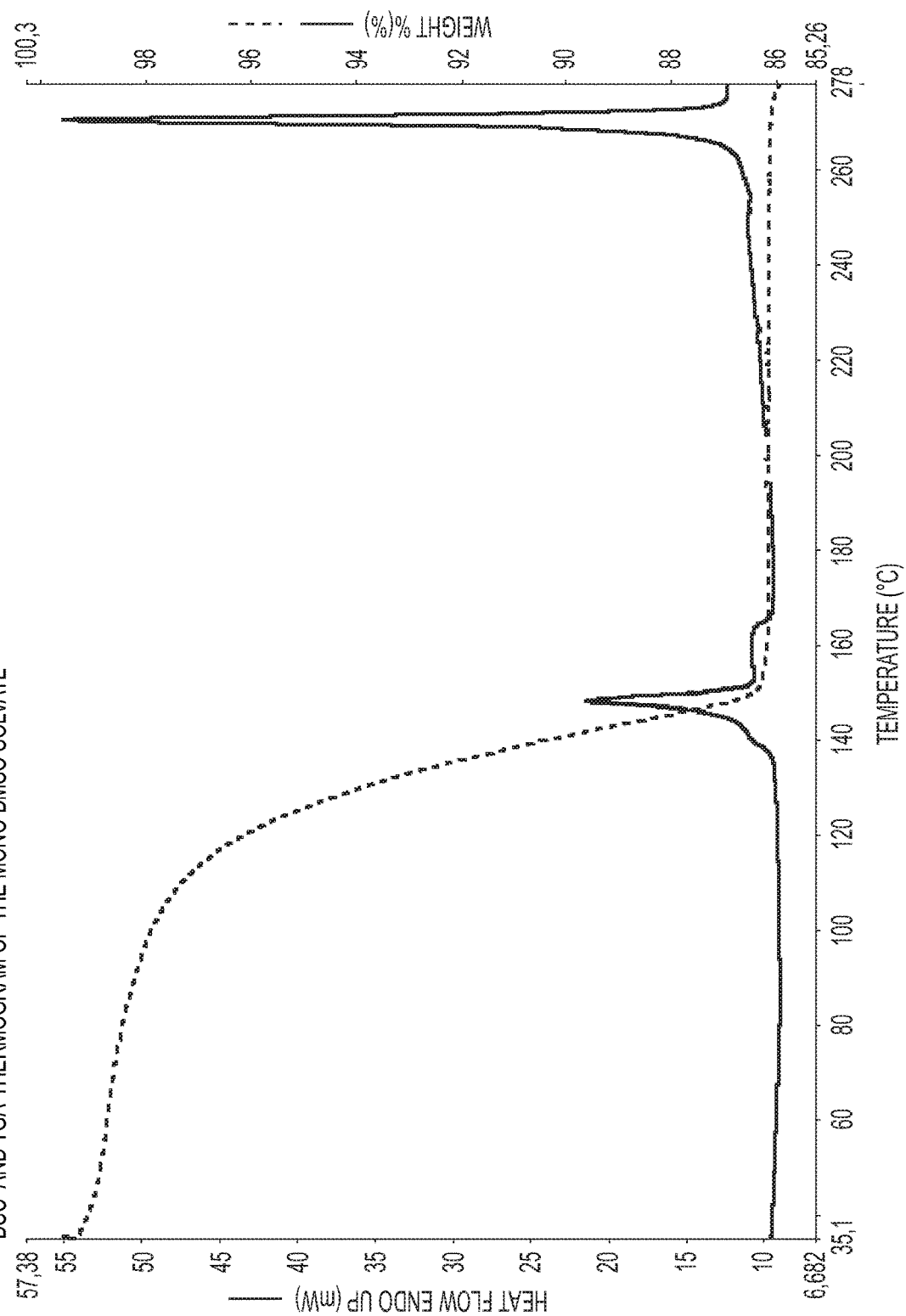

FIG. 8: DSC- and TGA-Thermogram of the mono-DMSO solvate

Figure 9:
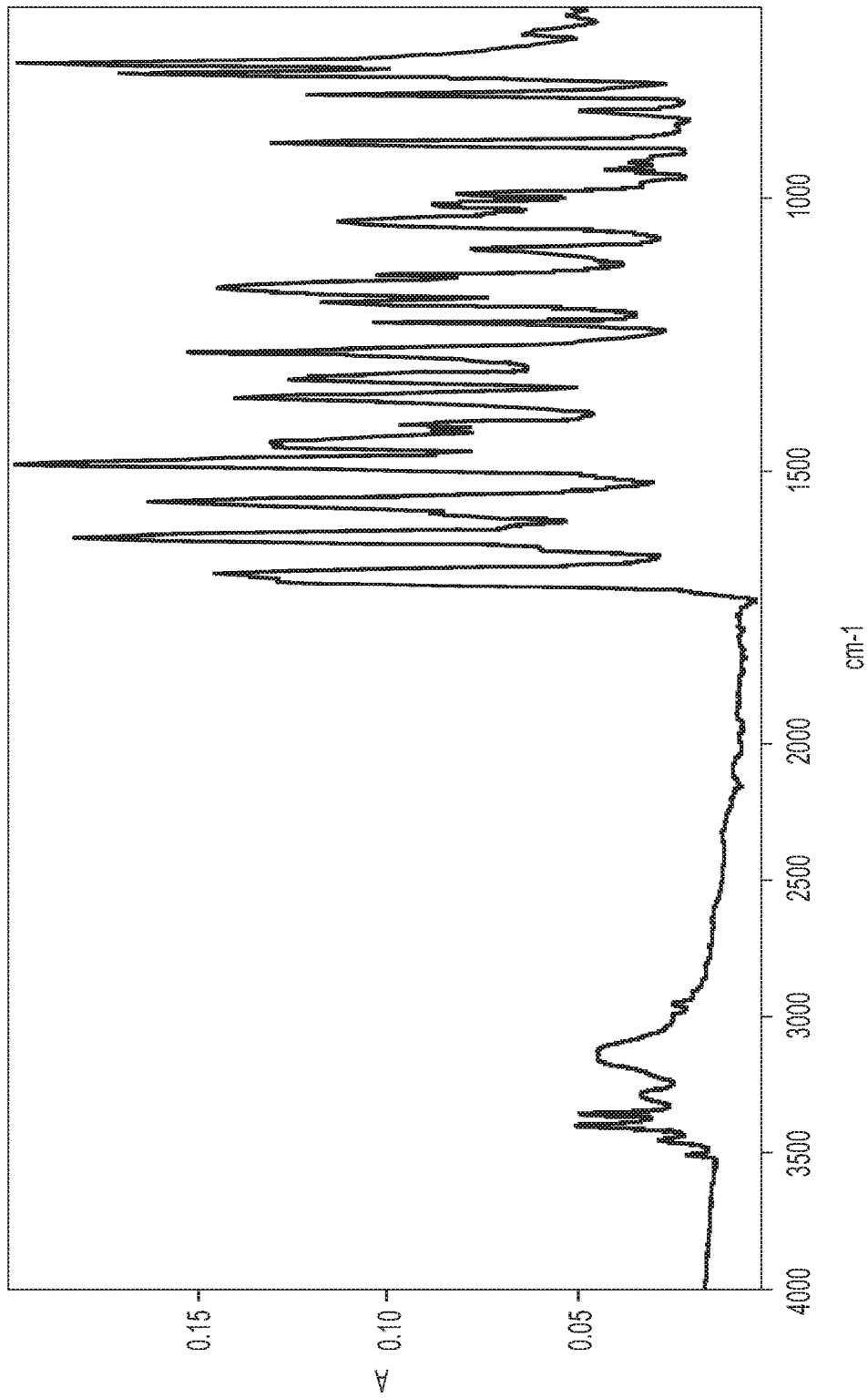

FIG. 9: IR-Spectrum (ATR) of the mono-DMSO solvate

Figure 10:
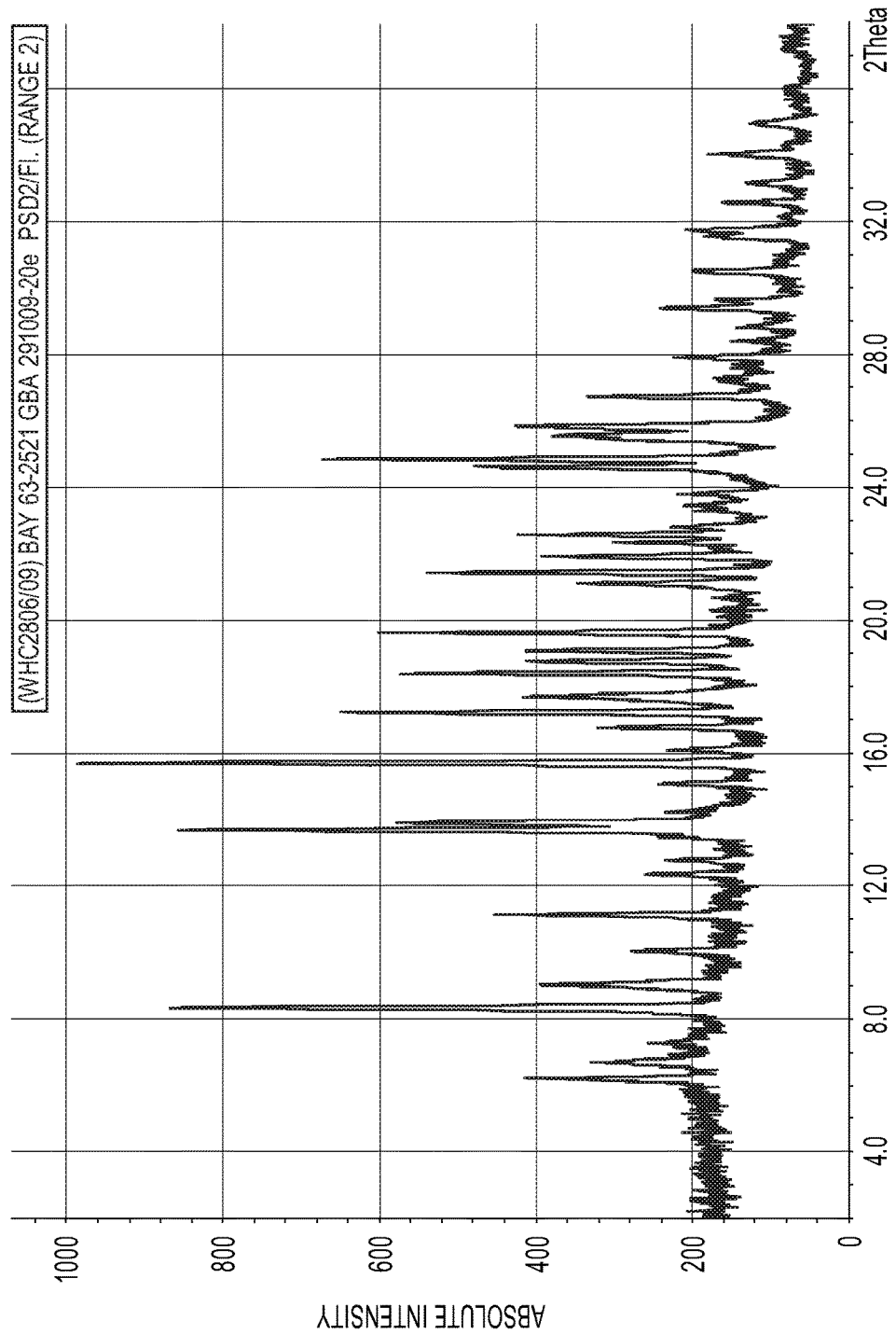

FIG. 10: X-Ray powder diffractogram of the sesqui-DMSO solvate

Figure 11:
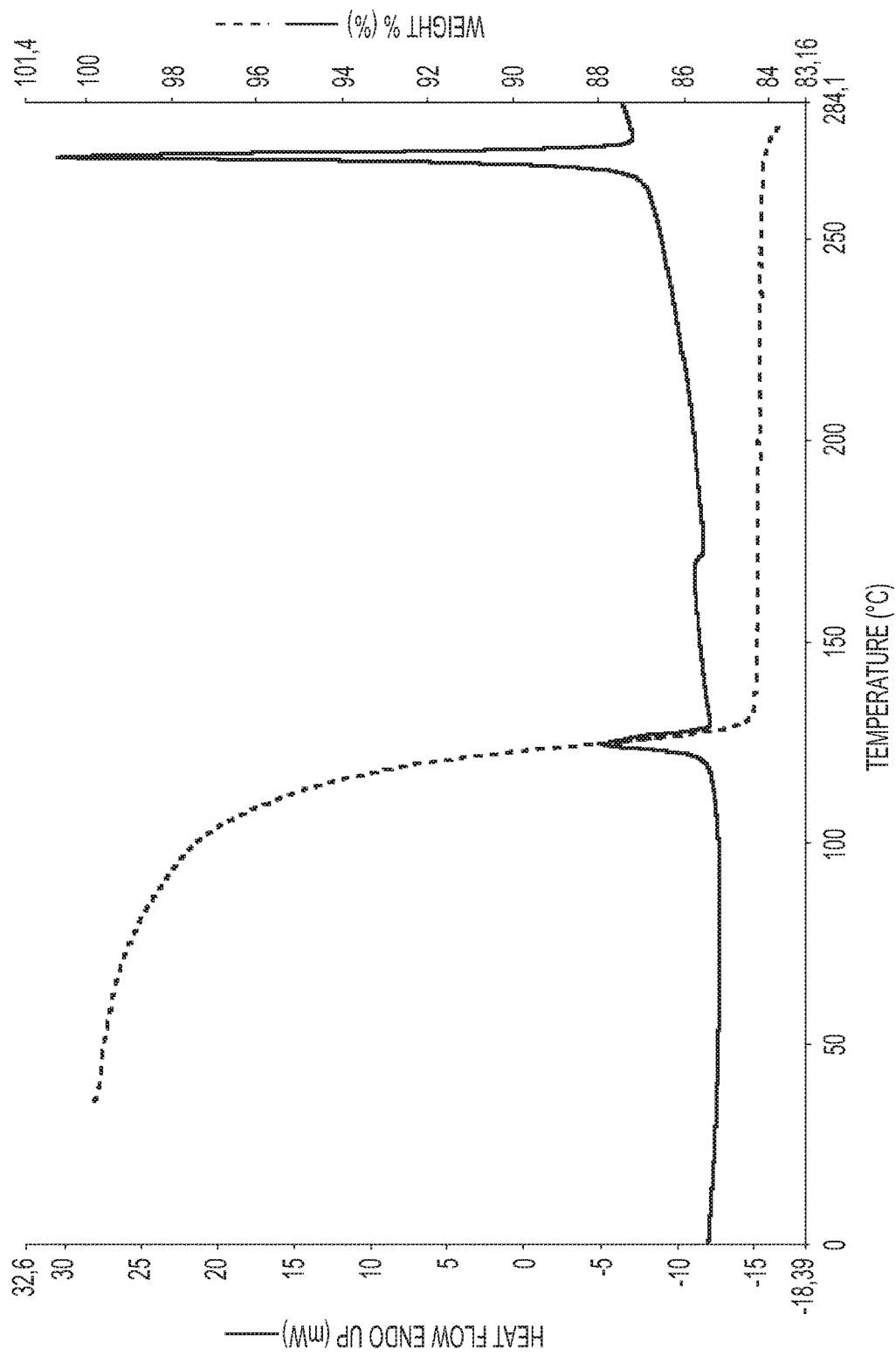

FIG. 11: DSC- and TGA-Thermogram of the sesqui-DMSO solvate

Figure 12:
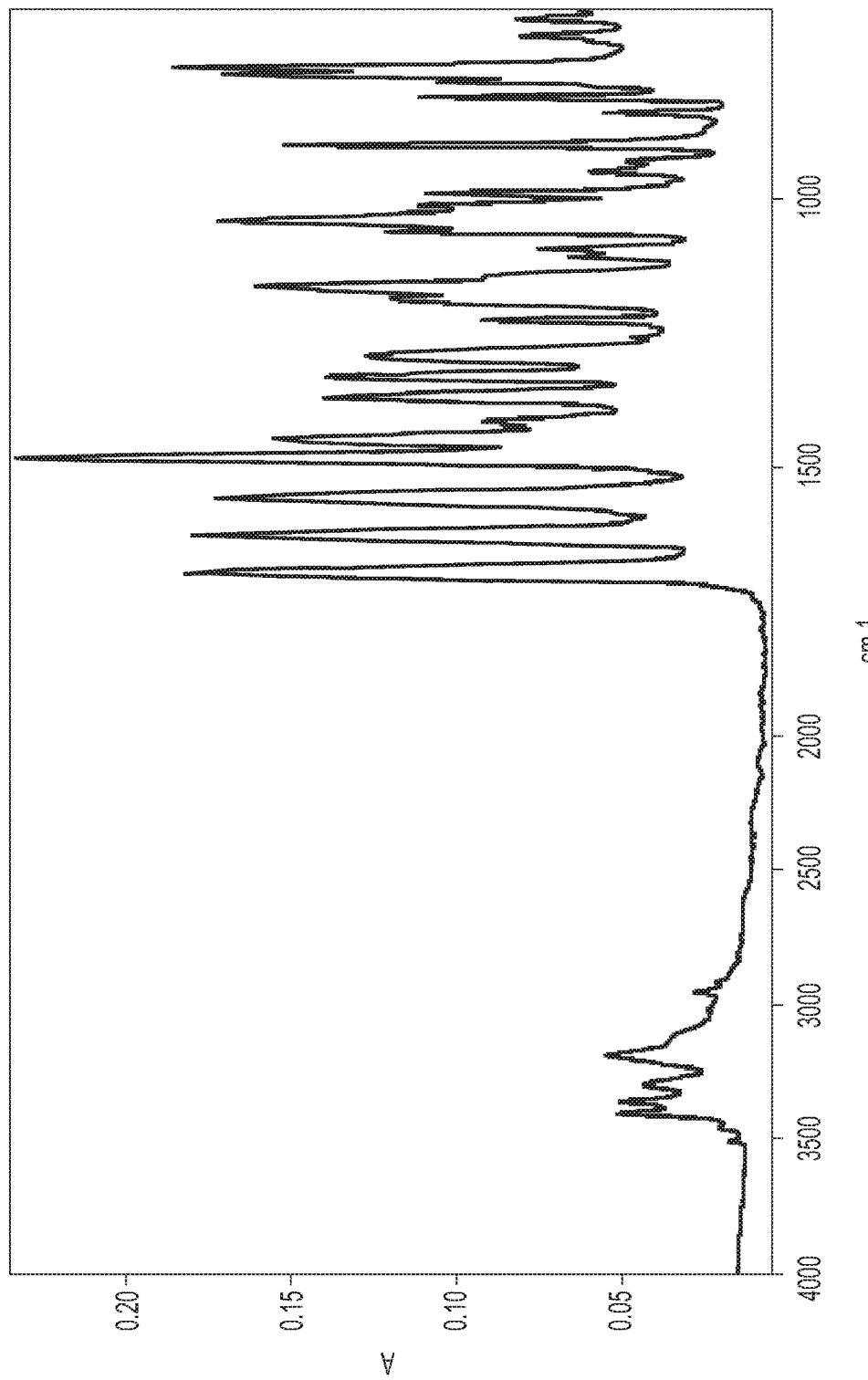

FIG. 12: IR-Spectrum (ATR) of the sesqui-DMSO solvate

Figure 13:
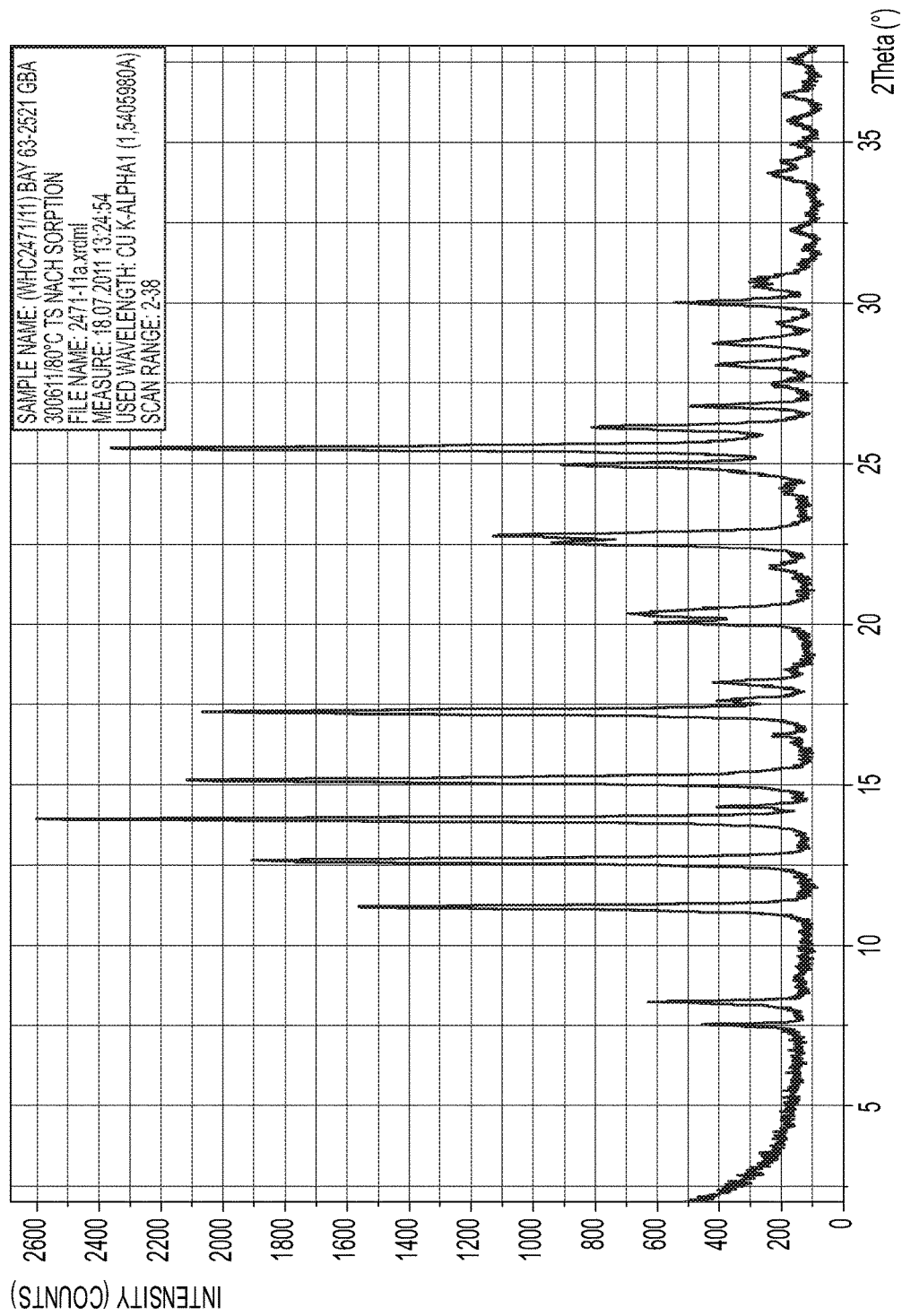

FIG. 13: X-Ray powder diffractogram of modification II

Figure 14:
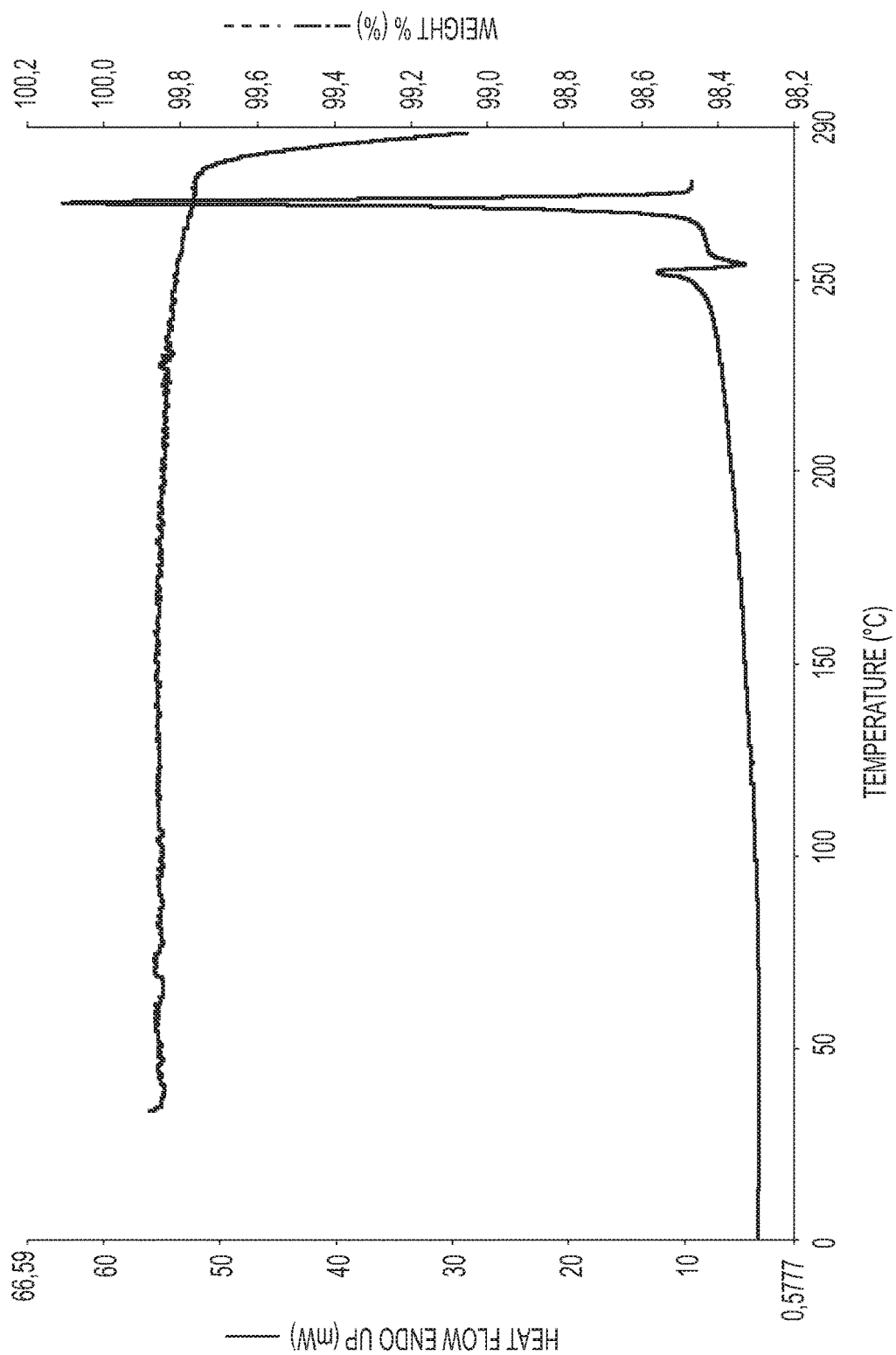

FIG. 14: DSC- and TGA-Thermogram of modification II

Figure 15:
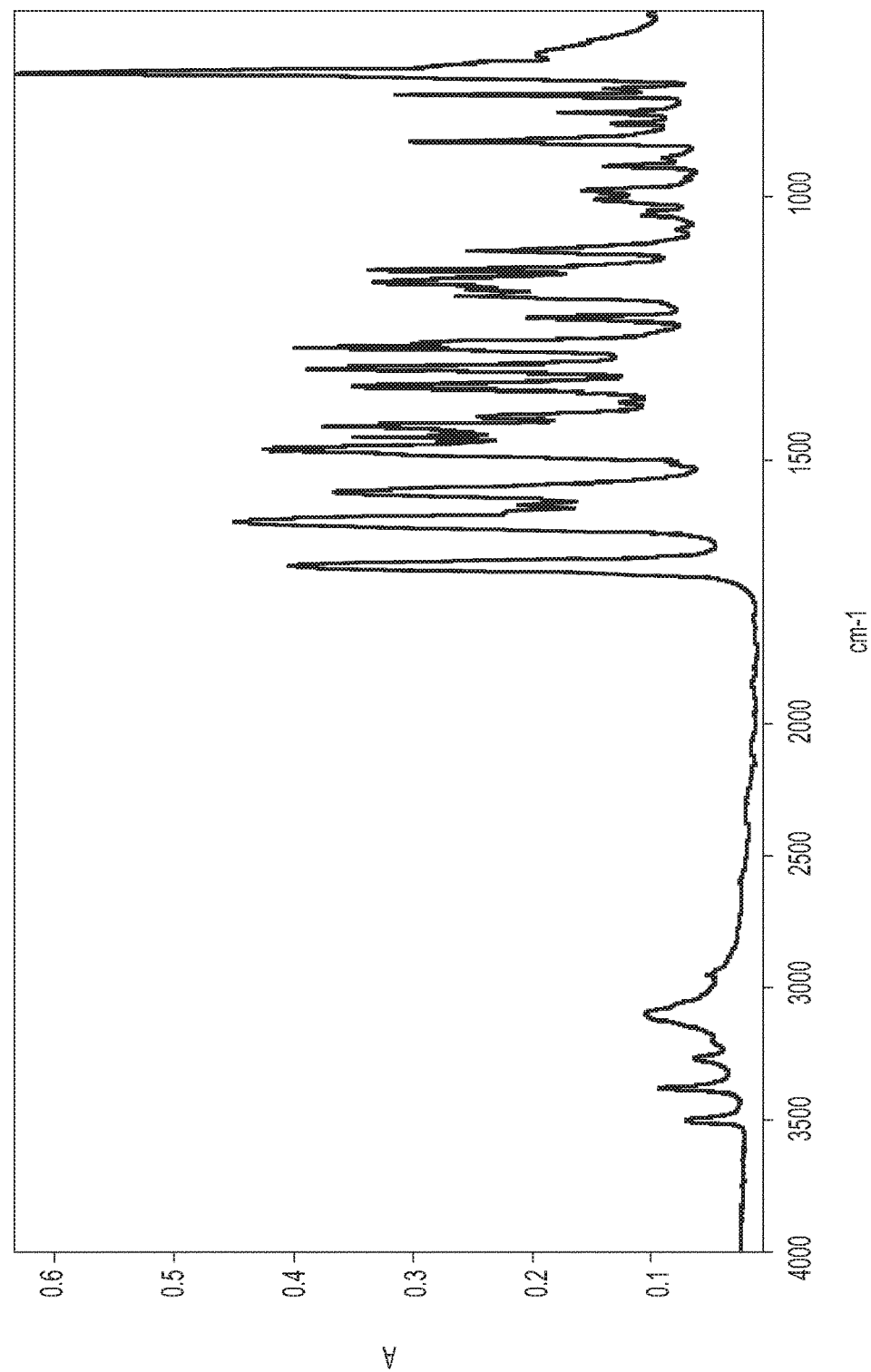

FIG. 15: IR-Spectrum (ATR) of modification II

Figure 16:
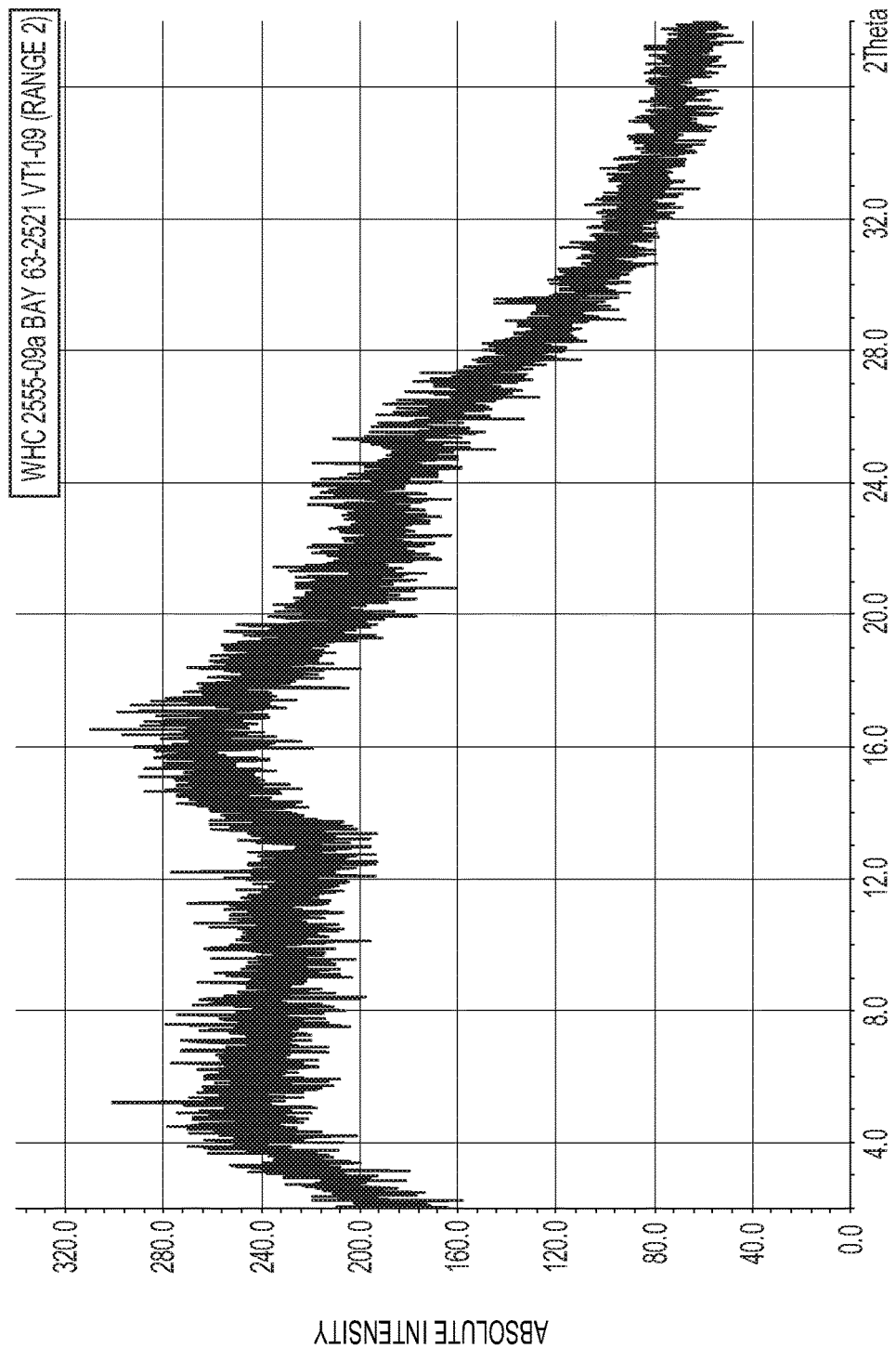

FIG. 16: X-Ray powder diffractogram of the amorphous form

Figure 17:
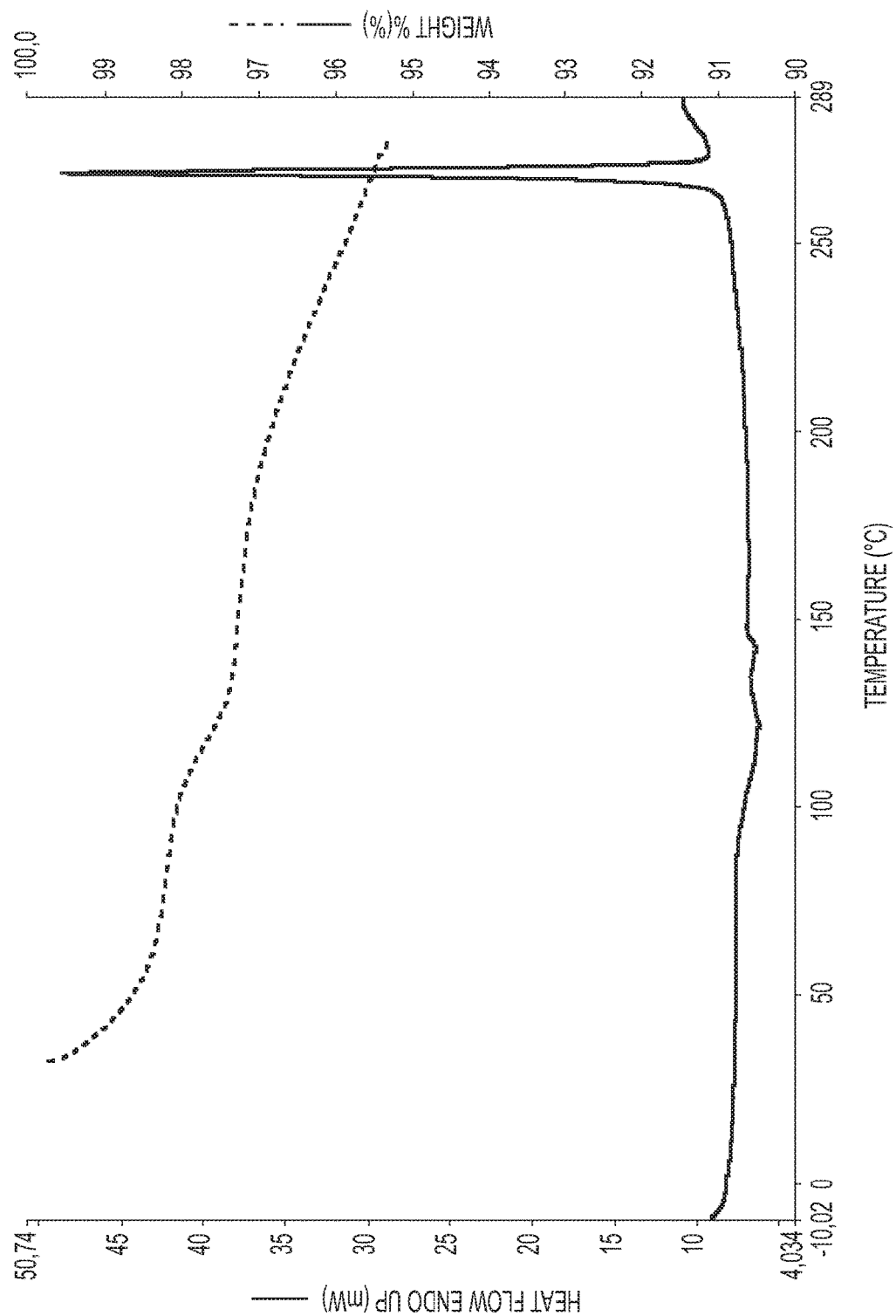

FIG. 17: DSC- and TGA-Thermogram of the amorphous form

FIG. 18: IR-Spectrum of the amorphous form

The compound of formula (I) in the Modification I can be characterized unambiguously by a X-Ray powder diffractogram comprising peak maxima of the 2 Theta angle of 6.7, 9.1, 14.3, 14.4, 17.8, 19.8, 20.2, 24.8, 25.6, 27.3, preferably by peak maxima of the 2 Theta angle of 6.7, 9.1 and 17.8.

The compound of formula (I) in the Modification II can be characterized unambiguously by a X-Ray powder diffractogram comprising peak maxima of the 2 Theta angle of 11.2, 12.6, 12.7, 13.9, 15.2, 17.3, 22.5, 22.8, 25.0, 25.5, preferably by peak maxima of the 2 Theta angle of 13.9, 17.3 and 25.5. The mono-DMSO solvate of the compound of formula (I) can be characterized unambiguously by a X-Ray powder diffractogram comprising peak maxima of the 2 Theta angle of 9.0, 10.8, 11.1, 11.2, 13.0, 15.5, 15.9, 16.0, 20.7, 25.6, preferably by peak maxima of the 2 Theta angle of 10.8, 15.5 and 20.7. The sesqui-DMSO solvate of the compound of formula (I) can be characterized unambiguously by a X-Ray powder diffractogram comprising peak maxima of the 2 Theta angle of 8.3, 8.4, 13.7, 13.9, 15.7, 17.2, 18.4, 19.6, 21.4, 24.9, preferably by peak maxima of the 2 Theta angle of 8.3, 13.7 and 15.7. The ¼-Ethylacetate solvate of the compound of formula (I) can be characterized unambiguously by a X-Ray powder diffractogram comprising peak maxima of the 2 Theta angle of 6.7, 8.3, 8.7, 12.9, 14.2, 17.8, 19.3, 24.0, 25.1, 26.7, preferably by peak maxima of the 2 Theta angle of 8.7, 17.8 and 26.7. The compound of formula (I) in the Modification I can be characterized unambiguously by an IR-spectrogram comprising peak maxima at a wave number of 3454, 3360, 3273, 3103, 1688, 1622, 1559, 1284, 1193, 989, 777, preferably by peak maxima at a waver number of 3360, 1688, and 1622. The compound of formula (I) in the Modification II can be characterized unambiguously by an IR-spectrogram comprising peak maxima at a wave number of 3498, 3382, 3269, 3104, 1704, 1622, 1586, 1563, 1326, 1288, 1106, preferably by peak maxima at a waver number of 3382, 1704, and 1622. The mono-DMSO solvate of the compound of formula (I) can be characterized unambiguously by an IR-spectrogram fractogram comprising peak maxima at a wave number of 3401, 3361, 3295, 3168, 1702, 1626, 1560, 1333, 1286, 1042, 751, preferably by peak maxima at a waver number of 3295, 1702, and 1626. The sesqui-DMSO solvate of the compound of formula (I) can be characterized unambiguously by an IR-spectrogram comprising peak maxima at a wave number of 3407, 3361, 3300, 3190, 1698, 1629, 1558, 1293, 1043, 770, 757, preferably by peak maxima at a waver number of 3300, 1698, and 1629. The ¼-Ethylacetate solvate of the compound of formula (I) can be characterized unambiguously by an IR-spectrogram comprising peak maxima at a wave number of 1732, 1702, and 1619.3363, 3275, 1732, 1702, 1619, 1560, 1457, 1246, 899, 810, 771, preferably by peak maxima at a waver number of 1732, 1702, and 1619.

Method for Treatment:

The compounds according to the invention may have useful pharmacological properties and may be employed for the prevention and treatment of disorders in humans and animals. The compounds according to the invention may open up a further treatment alternative and may therefore be an enrichment of pharmacy.

The compounds according to the invention may bring about vessel relaxation and inhibition of thrombocyte aggregation and lead to a lowering of blood pressure and to an increase in coronary blood flow. These effects are due to direct stimulation of soluble guanylate cyclase and an increase in intracellular cGMP. Moreover, the compounds according to the invention may intensify the action of substances that raise the cGMP level, for example EDRF (endothelium-derived relaxing factor), NO donors, protoporphyrin IX, arachidonic acid or phenylhydrazine derivatives.

The compounds according to the invention may be suitable for the treatment and/or prophylaxis of cardiovascular, pulmonary, thromboembolic and fibrotic diseases.

The compounds according to the invention may therefore be used in medicinal products for the treatment and/or prophylaxis of cardiovascular diseases, for example high blood pressure (hypertension), resistant hypertension, acute and chronic heart failure, coronary heart disease, stable and unstable angina pectoris, peripheral and cardiac vascular diseases, arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV junction extrasystoles, sick-sinus syndrome, syncopes, AV-node reentry tachycardia, Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction (PVC)), for the treatment and/or prophylaxis of thromboembolic diseases and ischaemias such as myocardial ischaemia, myocardial infarction, stroke, cardiac hypertrophy, transient ischaemic attacks, preeclampsia, inflammatory cardiovascular diseases, spasms of the coronary arteries and peripheral arteries, development of oedema, for example pulmonary oedema, cerebral oedema, renal oedema or oedema due to heart failure, peripheral perfusion disturbances, reperfusion injury, arterial and venous thromboses, microalbuminuria, myocardial insufficiency, endothelial dysfunction, for preventing restenoses such as after thrombolysis therapies, percutaneous transluminal angioplasty (PTA), transluminal coronary angioplasty (PTCA), heart transplant and bypass operations, and micro- and macrovascular damage (vasculitis), increased level of fibrinogen and of low-density LDL and increased concentrations of plasminogen activator inhibitor 1 (PAI-1), and for the treatment and/or prophylaxis of erectile dysfunction and female sexual dysfunction.

In the sense of the present invention, the term heart failure comprises both acute and chronic manifestations of heart failure, as well as more specific or related forms of disease such as acute decompensated heart failure, right ventricular failure, left ventricular failure, total heart failure, ischaemic cardiomyopathy, dilatated cardiomyopathy, hypertrophic cardiomyopathy, idiopathic cardiomyopathy, congenital heart defects, heart failure with valvular defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined valvular defects, heart muscle inflammation (myocarditis), chronic myocarditis, acute myocarditis, viral myocarditis, diabetic heart failure, alcoholic cardiomyopathy, storage cardiomyopathies, diastolic heart failure and also systolic heart failure and acute phases of an existing chronic heart failure (worsening heart failure).

In addition, the compounds according to the invention may also be used for the treatment and/or prophylaxis of arteriosclerosis, disturbances of lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity, and combined hyperlipidaemias and metabolic syndrome.

Moreover, the compounds according to the invention may be used for the treatment and/or prophylaxis of primary and secondary Raynaud phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds according to the invention may be suitable for treating urological diseases, for example benign prostatic syndrome (BPS), benign prostatic hyperplasia (BPH), benign prostatic enlargement (BPE), bladder outlet obstruction (BOO), lower urinary tract syndromes (LUTS, including feline urological syndrome (FUS)), diseases of the urogenital system including neurogenic overactive bladder (OAB) and (IC), urinary incontinence (UI) for example mixed, urge, stress, or overflow incontinence (MUI, UUI, SUI, OUI), pelvic pains, benign and malignant diseases of the organs of the male and female urogenital system.

Furthermore, the compounds according to the invention may be suitable for the treatment and/or prophylaxis of kidney diseases, in particular acute and chronic renal insufficiency, and acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex—induced kidney diseases, nephropathy induced by toxic substances, contrast medium—induced nephropathy, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally increased blood concentrations of urea, nitrogen, potassium and/or creatinine, altered activity of renal enzymes such as e.g. glutamyl synthetase, altered urine osmolarity or urine volume, increased microalbuminuria, macroalbuminuria, lesions of glomeruli and arterioles, tubular dilatation, hyperphosphataemia and/or need for dialysis. The present invention also comprises the use of the compounds according to the invention for the treatment and/or prophylaxis of sequelae of renal insufficiency, for example pulmonary oedema, heart failure, uraemia, anaemia, electrolyte disturbances (e.g. hyperkalaemia, hyponatraemia) and disturbances in bone and carbohydrate metabolism.

Furthermore, the compounds according to the invention may also be suitable for the treatment and/or prophylaxis of asthmatic diseases, pulmonary arterial hypertension (PAH) and other forms of pulmonary hypertension (PH), comprising pulmonary hypertension associated with left ventricular disease, HIV, sickle cell anaemia, thromboembolism (CTEPH), sarcoidosis, COPD or pulmonary fibrosis, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF).

The compounds described in the present invention may also be active substances for controlling diseases in the central nervous system that are characterized by disturbances of the NO/cGMP system. In particular, they may be suitable for improving perception, capacity for concentration, capacity for learning or memory performance after cognitive disturbances, such as occur in particular in situations/diseases/syndromes such as mild cognitive impairment, age-related learning and memory disturbances, age-related memory loss, vascular dementia, head injury, stroke, post-stroke dementia, post-traumatic head injury, general disturbances of concentration, disturbances of concentration in children with learning and memory problems, Alzheimer's disease, Lewy body dementia, dementia with frontal lobe degeneration including Pick's syndrome, Parkinson's disease, progressive nuclear palsy, dementia with corticobasal degeneration, amyotrophic lateral sclerosis (ALS), Huntington's disease, demyelination, multiple sclerosis, thalamic degeneration, Creutzfeldt-Jakob dementia, HIV-dementia, schizophrenia with dementia or Korsakoff psychosis. They may also be suitable for the treatment and/or prophylaxis of diseases of the central nervous system such as anxiety, tension and depression, CNS-related sexual dysfunctions and sleep disturbances and for controlling pathological eating disorders and use of luxury foods and addictive drugs.

Furthermore, the compounds according to the invention may also be suitable for controlling cerebral perfusion and are effective agents for combating migraines. They may also be suitable for the prophylaxis and control of consequences of cerebral infarctions (apoplexia cerebri) such as stroke, cerebral ischaemias and head injury. The compounds according to the invention may also be used for controlling pain states and tinnitus.

In addition, the compounds according to the invention may also possess anti-inflammatory action and may therefore be used as anti-inflammatory agents for the treatment and/or prophylaxis of sepsis (SIRS), multiple organ failure (MODS, MOF), inflammatory diseases of the kidney, chronic intestinal inflammations (IBD, Crohn's disease, UC), pancreatitis, peritonitis, rheumatoid diseases, inflammatory skin diseases and inflammatory eye diseases.

Moreover, the compounds according to the invention may also be used for the treatment and/or prophylaxis of auto-immune diseases.

Furthermore, the compounds according to the invention may be suitable for the treatment and/or prophylaxis of fibrotic diseases of the internal organs, for example of the lung, heart, kidney, bone marrow and in particular of the liver, and dermatological fibroses and fibrotic diseases of the eye. In the sense of the present invention, the term fibrotic diseases comprises in particular the following terms: hepatic fibrosis, hepatic cirrhosis, pulmonary fibrosis, endomyocardial fibrosis, nephropathy, glomerulonephritis, interstitial renal fibrosis, fibrotic lesions as a consequence of diabetes, bone marrow fibrosis and similar fibrotic diseases, scleroderma, morphea, keloids, hypertrophic scars (including after surgery), naevi, diabetic retinopathy, proliferative vitreoretinopathy and connective tissue diseases (e.g. sarcoidosis).

Furthermore, the compounds according to the invention may be suitable for controlling postoperative scarring, e.g. as a result of glaucoma operations.

The compounds according to the invention may also be used cosmetically for ageing and keratinizing skin.

Moreover, the compounds according to the invention may also be suitable for the treatment and/or prophylaxis of hepatitis, neoplasms, osteoporosis, glaucoma and gastroparesis.

In some embodiments, the present invention further relates to the use of the compounds according to the invention for the treatment and/or prophylaxis of diseases, in particular the aforementioned diseases.

In some embodiments, the present invention further relates to the use of the compounds according to the invention for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

In some embodiments, the present invention further relates to the compounds according to the invention for use in a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

In some embodiments, the present invention further relates to the use of the compounds according to the invention for producing a medicinal product for the treatment and/or prophylaxis of diseases, in particular the aforementioned diseases.

In some embodiments, the present invention further relates to the use of the compounds according to the invention for producing a medicinal product for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis.

In some embodiments, the present invention further relates to a method for the treatment and/or prophylaxis of diseases, in particular the aforementioned diseases, using an effective amount of at least one of the compounds according to the invention.

In some embodiments, the present invention further relates to a method for the treatment and/or prophylaxis of heart failure, angina pectoris, hypertension, pulmonary hypertension, ischaemias, vascular diseases, renal insufficiency, thromboembolic diseases, fibrotic diseases and arteriosclerosis, using an effective amount of at least one of the compounds according to the invention.

The compounds according to the invention can be used alone or in combination with other active substances if necessary. The present invention further relates to medicinal products containing at least one of the compounds according to the invention and one or more further active substances, in particular for the treatment and/or prophylaxis of the aforementioned diseases. As suitable combination active substances, we may mention for example and preferably:
- organic nitrates and NO-donors, for example sodium nitroprusside, nitroglycerin, isosorbide mononitrate, isosorbide dinitrate, molsidomine or SIN-1, and inhalational NO;
- compounds that inhibit the degradation of cyclic guanosine monophosphate (cGMP), for example inhibitors of phosphodiesterases (PDE) 1, 2 and/or 5, in particular PDE-5 inhibitors such as sildenafil, vardenafil and tadalafil;
- antithrombotic agents, for example and preferably from the group of platelet aggregation inhibitors, anticoagulants or profibrinolytic substances;
- active substances for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or
- active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a loop diuretic, for example furosemide, torasemide, bumetanide and piretanide, with potassium-sparing diuretics for example amiloride and triamterene, with aldosterone antagonists, for example spironolactone, potassium canrenoate and eplerenone and thiazide diuretics, for example hydrochlorothiazide, chlorthalidone, xipamide, and indapamide.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably dalcetrapib, BAY 60-5521, anacetrapib or CETP-vaccine (CETi-1).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

Pharmaceutical Compositions:

This invention also relates to pharmaceutical compositions containing one of the forms of the compound of the formula (I) or a mixture thereof. These compositions may be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of one of the forms of the compound of the formula (I) or a mixture thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The forms of the compound of the formula (I) of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the form of the compound of the formula (I) of the present invention can be formulated into solid or liquid preparations such as solid dispersion, capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the form of the compound of the formula (I) of the present invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Dosage of the Pharmaceutical Compositions of the Present Invention:

Based upon standard laboratory techniques known to evaluate compounds useful for the treatment of disorders, by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.0001 mg/kg to about 20 mg/kg, and preferably from about 0.001 mg/kg to about 2 mg/kg body weight per day. A unit dosage may contain from about 0.05 mg to about 150 mg of active ingredient, and can be administered one or more times per day.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The weight data in the tests and examples which follow are, unless stated otherwise, percentages by weight; parts are parts by weight. Solvent ratios, dilution ratios and concentration data of liquid/liquid solutions are based on each case on the volume.

WORKING EXAMPLES

DSC thermograms were recorded using Differential Scanning calorimeters (model DSC7, Pyris-1 or Diamond) from Perkin-Elmer. The measurements were performed with a heating rate of 20 Kmin$^{-1}$ using non-gastight aluminium pans. Flow gas was nitrogen. There was no sample preparation.

TGA thermograms were recorded using thermobalances (model TGA7 and Pyris 1) from Perkin-Elmer. The measurements were performed with a heating rate of 10 Kmin$^{-1}$ using open platinum pans. Flow gas was nitrogen. There was no sample preparation.

X-Ray diffraction patterns were recorded at room temperature using XRD-diffractometers X'Pert PRO (PANalytical) and STOE STADI-P (radiation Cu K alpha 1, wavelength 1.5406 Å). There was no sample preparation.

Raman spectra were recorded at room temperature using FT-Raman-spectrophotometers (model RFS 100 and MultiRam) from Bruker. Resolution was 2 cm$^{-1}$. Measurements were performed in glass vials or aluminium discs. There was no sample preparation.

IR-ATR-spectra were recorded at room temperature using a FT-IR-spectrophotometer one with universal diamond ATR device from Perkin-Elmer. Resolution was 4 cm$^{-1}$. There was no sample preparation.

Example 1

Preparation of Purified methyl 4,6-diamino-2-[1-(2-fluorobenzyl)-1H-pyrazolo[3,4-b]pyridin-3-yl]-5-pyrimidinyl(methyl)carbamate (I)

The entire amount of the product of the formula (II) prepared in the Example 6 of WO 2011/064171 was stirred in 135 ml of ethyl acetate at reflux (about 78° C.) for 1 h and cooled to about 25° C. The solid was filtered off with suction, washed with a total of 36 ml of ethyl acetate and dried under reduced pressure. The weight was 7.6 g or 93.8% of theory. The content of the product was markedly above 98% by weight (HPLC). As solvent, ethyl acetate was present in an amount of about 0.2%. The DMSO content was below 0.1%.

Example 2

Preparation and Analytical Characterization of methyl {4,6-diamino-2-[1-(2-fluorobenzyl)-1H-pyrazolo[3,4-b]pyridin-3-yl]pyrimidin-5-yl}methylcarbamate sulphinyldimethane (Compound According to Formula (I) as mono-DMSO Solvate)

14.8 g of a crude product of the formula (I) were dissolved in 28.9 g of DMSO and 11.85 g of ethyl acetate at about 94°

C. 1.5 g of activated carbon Norit A-Supra and a further 11.85 g of ethyl acetate were then added, the mixture was stirred at reflux (88-90° C.) for 1 h and the hot mixture was then filtered to remove the activated carbon. The solid, some of which had already precipitated, was re-dissolved by warming to about 78° C., and the solution was then allowed to cool slowly. The precipitated solid was filtered off with suction at RT, washed three times with in each case 50 ml of ethyl acetate and dried in a drying cabinet at 30° C. for 18 h. This gave 9.2 g or 52.5% of theory of a slightly yellowish crystal powder of the compound of the formula (II).

HPLC: 99.90 area % (without taking the DMSO into account)

DMSO (GC): 14.7% by weight $^1$H-NMR (400 MHz in DMF-$d_7$):

d=2.59 (s, about 6H, 2 $CH_3$ at DMSO), 3.13 (s, 3H, N—$CH_3$), 3.58+3.67 (two s, 3H, hindered rotation at O—$CH_3$), 5.91 (s, 2H, —$CH_2$—), 6.53 (s, 4H, 2-$NH_2$), 7.05-7.40 (m, 5H, 4 aromatic H at the o-fluorobenzyl substituent and 1H at the pyrido ring meta to the pyrido nitrogen), 8.60 (dd, 1H, at the pyrido ring ortho to the pyrido nitrogen), 9.12 (dd, 1H, at the pyrido ring para to the pyrido nitrogen).

Elemental Analysis:

| found | C: 52.2% | calculated | C: 52.79% |
|---|---|---|---|
|  | H: 4.9% |  | H: 5.03% |
|  | N: 22.7% |  | N: 22.39% |

Example 3

Preparation of methyl {4,6-diamino-2-[1-(2-fluorobenzyl)-1H-pyrazolo[3,4-b]pyridin-3-yl]pyrimidin-5-yl}methylcarbamate of Formula (I) in its Modification II 0.5 g of the compound according to formula (I) as mono DMSO solvate was tempered for 2 days at 80° C.

Example 4

Preparation of methyl {4,6-diamino-2-[1-(2-fluorobenzyl)-1H-pyrazolo[3,4-b]pyridin-3-yl]pyrimidin-5-yl}methylcarbamate of Formula (I) as Sesqui-DMSO Solvate 160 mg of the compound according to formula (I) in its amorphous form were suspended in 2 ml Ethylacetat:DMSO (1:1). The suspension was stirred in a sealed container for three weeks at room temperature. The residue was filtered and dried at room temperature.

Example 5

Preparation of methyl {4,6-diamino-2-[1-(2-fluorobenzyl)-1H-pyrazolo[3,4-b]pyridin-3-yl]pyrimidin-5-yl}methylcarbamate of Formula (I) in its Amorphous Form 0.5 g of the compound according to formula (I) in its Modification (I) were ground in a swing mill for 30 min with a vibration of 30 swings per second.

Example 6

Preparation of methyl {4,6-diamino-2-[1-(2-fluorobenzyl)-1H-pyrazolo[3,4-b]pyridin-3-yl]pyrimidin-5-yl}methylcarbamate of Formula (I) as ¼ Ethyl Acetate Solvate 9.6 g of compound according to formula (I) was stirred in 135 ml of ethyl acetate at reflux (about 78° C.) for 1 h and cooled to about 25° C. The solid was filtered off with suction, washed with a total of 36 ml of ethyl acetate and dried under reduced pressure. The weight was 7.6 g or 93.8% of theory. The content of the product was markedly above 98% by weight (HPLC). As solvent, ethyl acetate was present in an amount of about 0.2%. The DMSO content was below 0.1%.

In this reaction, an ethyl acetate containing solid polymorph (¼-ethyl acetate-solvate) may be formed and isolated.

Example 7

Pharmaceutical Formulation of methyl {4,6-diamino-2-[1-(2-fluorobenzyl)-1H-pyrazolo[3,4-b]pyridin-3-yl]pyrimidin-5-yl}methylcarbamate (0.5 mg)

| Composition | Reference to standard | Function | Amount [mg] |
|---|---|---|---|
| Drug substance | | | |
| Riociguat micronized | specification | drug substance | 0.50 |
| Excipients | | | |
| Cellulose microcrystalline | Ph. Eur., NF, Ph. Jap. | filler | 35.00 |
| Crospovidone | Ph. Eur., NF, JPE | disintegrant | 6.00 |
| Hypromellose 5 cP (syn. Hydroxypropylmethylcellulose 2910) | Ph. Eur., USP, Ph. Jap. | binder | 3.00 |
| Lactose monohydrate | Ph. Eur., NF, Ph. Jap. | filler | 39.80 |
| Magnesium stearate | Ph. Eur., NF, Ph. Jap. | lubricant | 0.60 |
| Sodium laurilsulfate | Ph. Eur., NF, Ph. Jap. | wetting agent | 0.10 |
| Weight (tablet) | | | 85.00 |
| Film-coating | | | |
| Hydroxypropylcellulose | Ph. Eur., NF, Ph. Jap. | film forming agent | 1.10 |
| Hypromellose 3 cP (syn. Hydroxypropylmethylcellulose 2910) | Ph. Eur., USP, Ph. Jap. | film forming agent | 0.36 |

-continued

| Composition | Reference to standard | Function | Amount [mg] |
|---|---|---|---|
| Propylene glycol | Ph. Eur., USP | plasticizer | 0.21 |
| Titanium dioxide | Ph. Eur., USP, Ph. Jap., Directive 2008/128/EC | color pigment | 0.83 |
| Weight (film-coating) | | | 2.5 |
| Weight (coated tablet) | | | 87.5 |

Example 8

Pharmaceutical Formulation of methyl {4,6-di-amino-2-[1-(2-fluorobenzyl)-1H-pyrazolo[3,4-b]pyridin-3-yl]pyrimidin-5-yl}methylcarbamate (1.0 mg)

| Composition | Reference to standard | Function | Amount [mg] |
|---|---|---|---|
| *Drug substance* | | | |
| Riociguat micronized | specification | drug substance | 1.00 |
| *Excipients* | | | |
| Cellulose microcrystalline | Ph. Eur., NF, Ph. Jap. | filler | 35.00 |
| Crospovidone | Ph. Eur., NF, JPE | disintegrant | 6.00 |
| Hypromellose 5 cP (syn.: Hydroxypropylmethylcellulose 2910) | Ph. Eur., USP, Ph. Jap. | binder | 3.00 |
| Lactose monohydrate | Ph. Eur., NF, Ph. Jap. | filler | 39.20 |
| Magnesium stearate | Ph. Eur., NF, Ph. Jap. | lubricant | 0.60 |
| Sodium laurilsulfate | Ph. Eur., NF, Ph. Jap. | wetting agent | 0.20 |
| Weight (tablet) | | | 85.00 |
| *Film-coating* | | | |
| Hydroxypropylcellulose 1.10 | Ph. Eur., NF, Ph. Jap. | film forming agent | |
| Hypromellose 3 cP (syn. Hydroxypropylmethylcellulose 2910) | Ph. Eur., USP, Ph. Jap. | film forming agent | 0.36 |
| Propylene glycol | Ph. Eur., USP | plasticizer | 0.21 |
| Titanium dioxide | Ph. Eur., USP, Ph. Jap., Directive 2008/128/EC | color pigment | 0.82 |
| Ferric oxide yellow | NF, JPE, Directive 2008/128/EC | color pigment | 0.01 |
| Weight (film-coating) | | | 2.50 |
| Weight (coated tablet) | | | 87.50 |

Example 9

Pharmaceutical Formulation of methyl {4,6-di-amino-2-[1-(2-fluorobenzyl)-1H-pyrazolo[3,4-b]pyridin-3-yl]pyrimidin-5-yl}methylcarbamate (1.5 mg)

| Composition | Reference to standard | Function | Amount [mg] |
|---|---|---|---|
| *Drug substance* | | | |
| Riociguat micronized | specification | drug substance | 1.50 |
| *Excipients* | | | |
| Cellulose microcrystalline | Ph. Eur., NF, Ph. Jap. | filler | 35.00 |
| Crospovidone | Ph. Eur., NF, JPE | disintegrant | 6.00 |
| Hypromellose 5 cP (syn.: Hydroxypropylmethylcellulose 2910) | Ph. Eur., USP, Ph. Jap. | binder | 3.00 |
| Lactose monohydrate | Ph. Eur., NF, Ph. Jap. | filler | 38.70 |
| Magnesium stearate | Ph. Eur., NF, Ph. Jap. | lubricant | 0.60 |
| Sodium laurilsulfate | Ph. Eur., NF, Ph. Jap. | wetting agent | 0.20 |
| Weight (tablet) | | | 85.00 |

| Composition | Reference to standard | Function | Amount [mg] |
|---|---|---|---|
| Film-coating | | | |
| Hydroxypropylcellulose | Ph. Eur., NF, Ph. Jap. | film forming agent | 1.10 |
| Hypromellose 3 cP (syn. Hydroxypropylmethylcellulose 2910)- | Ph. Eur., USP, Ph. Jap. | film forming agent | 0.36 |
| Propylene glycol | Ph. Eur., USP. | plasticizer | 0.21 |
| Titanium dioxide | Ph. Eur., USP, Ph. Jap., Directive 2008/128/EC | color pigment | 0.73 |
| Ferric oxide yellow | NF, JPE, Directive 2008/128/EC | color pigment | 0.10 |
| Weight (film-coating) | | | 2.50 |
| Weight (coated tablet) | | | 87.50 |

Example 10

Pharmaceutical Formulation of methyl {4,6-diamino-2-[1-(2-fluorobenzyl)-1H-pyrazolo[3,4-b]pyridin-3-yl]pyrimidin-5-yl}methylcarbamate (2.0 mg)

| Composition | Reference to standard | Function | Amount [mg] |
|---|---|---|---|
| Drug substance | | | |
| Riociguat micronized | specification | drug substance | 2.00 |
| Excipients | | | |
| Cellulose microcrystalline | Ph. Eur., NF, Ph. Jap. | filler | 35.00 |
| Crospovidone | Ph. Eur., NF, JPE | disintegrant | 6.00 |
| Hypromellose 5 cP (syn. Hydroxypropylmethylcellulose 2910) | Ph. Eur., USP, Ph. Jap. | binder | 3.00 |
| Lactose monohydrate | Ph. Eur., NF, Ph. Jap. | filler | 38.20 |
| Magnesium stearate | Ph. Eur., NF, Ph. Jap. | lubricant | 0.60 |
| Sodium laurilsulfate | Ph. Eur., NF, Ph. Jap. | wetting agent | 0.20 |
| Weight (tablet) | | | 85.00 |
| Film-coating | | | |
| Hydroxypropylcellulose | Ph. Eur., NF, Ph. Jap. | film forming agent | 1.10 |
| Hypromellose 3 cP (syn. Hydroxypropylmethylcellulose 2910) | Ph. Eur., USP, Ph. Jap. | film forming agent | 0.36 |
| Propylene glycol | Ph. Eur., USP | plasticizer | 0.21 |
| Titanium dioxide | Ph. Eur., USP, Ph. Jap., Directive 2008/128/EC | | |
| Ferric oxide yellow | NF, JPE, Directive 2008/128/EC | color pigment | 0.61 |
| Ferric oxide red | NF, JPE, Directive 2008/128/EC | color pigment | 0.20 |
| | | color pigment | 0.02 |
| Weight (film-coating) | | | 2.50 |
| Weight (coated tablet) | | | 87.50 |

Example 11

Pharmaceutical Formulation of methyl {4,6-diamino-2-[1-(2-fluorobenzyl)-1H-pyrazolo[3,4-b]pyridin-3-yl]pyrimidin-5-yl}methylcarbamate (2.5 mg)

| Composition | Reference to standard | Function | Amount [mg] |
|---|---|---|---|
| Drug substance | | | |
| Riociguat micronized | specification | drug substance | 2.50 |
| Excipients | | | |
| Cellulose microcrystalline | Ph. Eur., NF, Ph. Jap. | filler | 35.00 |
| Crospovidone | Ph. Eur., NF, JPE | disintegrant | 6.00 |

| Composition | Reference to standard | Function | Amount [mg] |
|---|---|---|---|
| Hypromellose 5 cP (syn. Hydroxypropylmethylcellulose 2910) | Ph. Eur., USP, Ph. Jap. | binder | 3.00 |
| Lactose monohydrate | Ph. Eur., NF, Ph. Jap. | filler | 37.70 |
| Magnesium stearate | Ph. Eur., NF, Ph. Jap. | lubricant | 0.60 |
| Sodium laurilsulfate | Ph. Eur., NF, Ph. Jap. | wetting agent | 0.20 |
| Weight (tablet) | | | 85.00 |
| Film-coating | | | |
| Hydroxypropylcellulose | Ph. Eur., NF, Ph. Jap. | film forming agent | 1.10 |
| Hypromellose 3 cP (syn. Hydroxypropylmethylcellulose 2910) | Ph. Eur., USP, Ph. Jap. | film forming agent | 0.36 |
| Propylene glycol | Ph. Eur., USP. | plasticizer | 0.21 |
| Titanium dioxide | Ph. Eur., USP, Ph. Jap., Directive 2008/128/EC | color pigment | 0.35 |
| Ferric oxide yellow | NF, JPE, Directive 2008/128/EC | color pigment | 0.40 |
| Ferric oxide red | NF, JPE, Directive 2008/128/EC | color pigment | 0.08 |
| Weight (film-coating) | | | 2.50 |
| Weight (coated tablet) | | | 87.50 |

TABLE 1

IR bands of the different crystalline forms
IR Bands [cm$^{-1}$]

| Mod. I | Mod. II | Mono-DMSO-Solvate | Sesqui-DMSO-Solvate | ¼-Ethylacetate-Solvate |
|---|---|---|---|---|
| 3508 | 3498 | 3401 | 3508 | 3506 |
| 3454 | 3382 | 3361 | 3407 | 3459 |
| 3360 | 3269 | 3295 | 3361 | 3363 |
| 3273 | 3104 | 3168 | 3300 | 3275 |
| 3103 | 2951 | 2950 | 3190 | 3116 |
| 2956 | 1704 | 1702 | 2956 | 2954 |
| 1688 | 1622 | 1645 | 1698 | 1732 |
| 1622 | 1586 | 1626 | 1629 | 1702 |
| 1559 | 1563 | 1578 | 1558 | 1619 |
| 1489 | 1491 | 1560 | 1485 | 1560 |
| 1483 | 1482 | 1490 | 1456 | 1484 |
| 1457 | 1457 | 1456 | 1447 | 1457 |
| 1437 | 1436 | 1446 | 1425 | 1438 |
| 1425 | 1419 | 1426 | 1416 | 1417 |
| 1417 | 1390 | 1415 | 1370 | 1366 |
| 1366 | 1362 | 1370 | 1333 | 1333 |
| 1333 | 1327 | 1335 | 1293 | 1282 |
| 1326 | 1288 | 1286 | 1227 | 1246 |
| 1284 | 1231 | 1276 | 1192 | 1229 |
| 1227 | 1189 | 1228 | 1169 | 1191 |
| 1193 | 1176 | 1193 | 1142 | 1167 |
| 1167 | 1164 | 1171 | 1111 | 1140 |
| 1140 | 1140 | 1142 | 1094 | 1094 |
| 1094 | 1106 | 1112 | 1063 | 1032 |
| 1034 | 1035 | 1092 | 1043 | 1008 |
| 1008 | 1007 | 1042 | 992 | 991 |
| 989 | 990 | 1015 | 950 | 935 |
| 935 | 943 | 993 | 901 | 899 |
| 899 | 896 | 947 | 840 | 840 |
| 840 | 861 | 901 | 811 | 810 |
| 810 | 842 | 845 | 784 | 771 |
| 799 | 809 | 810 | 770 | 753 |
| 777 | 796 | 784 | 757 | 700 |
| 771 | 769 | 775 | 698 | 637 |
| 756 | 631 | 751 | 667 | 592 |
| 700 | 590 | 692 | 572 | 572 |
| 594 | 573 | 622 | 512 | 512 |
| 512 | 559 | 593 | | |
| | 512 | | | |

TABLE 2

10 Major Peaks of IR bands of the different crystalline forms
IR Major Bands [cm$^{-1}$]

| Mod. I | Mod. II | Mono-DMSO-Solvate | Sesqui-DMSO-Solvate | ¼-Ethylacetate-Solvate |
|---|---|---|---|---|
| 3454 | 3498 | 3401 | 3407 | 3363 |
| 3360 | 3382 | 3361 | 3361 | 3275 |
| 3273 | 3269 | 3295 | 3300 | 1732 |
| 3103 | 3104 | 3168 | 3190 | 1702 |
| 1688 | 1704 | 1702 | 1698 | 1619 |
| 1622 | 1622 | 1626 | 1629 | 1560 |
| 1559 | 1586 | 1560 | 1558 | 1457 |
| 1284 | 1563 | 1333 | 1293 | 1246 |
| 1193 | 1326 | 1286 | 1043 | 899 |
| 989 | 1288 | 1042 | 770 | 810 |
| 777 | 1106 | 751 | 757 | 771 |

TABLE 3

X-Ray powder diffractogram of the different crystalline forms
Reflexes [Position °2Th.]

| Mod. I | Mod. II | Mono-DMSO-Solvate | Sesqui-DMSO-Solvate | ¼-Ethylacetate-Solvate |
|---|---|---|---|---|
| 6.7 | 7.6 | 5.5 | 6.2 | 6.7 |
| 9.1 | 8.3 | 6.2 | 6.7 | 7.2 |
| 13.7 | 10.3 | 6.7 | 7.3 | 8.3 |
| 13.8 | 11.2 | 7.5 | 8.3 | 8.7 |
| 14.3 | 12.6 | 8.4 | 8.4 | 9.1 |
| 14.4 | 12.7 | 9.0 | 9.0 | 10.9 |
| 17.8 | 13.9 | 10.3 | 10.1 | 12.9 |
| 18.4 | 14.3 | 10.8 | 11.1 | 13.3 |
| 18.7 | 15.2 | 11.1 | 12.4 | 13.7 |
| 18.9 | 16.6 | 11.2 | 12.8 | 13.8 |
| 19.8 | 17.3 | 12.4 | 13.7 | 14.2 |
| 20.2 | 17.6 | 12.8 | 13.9 | 14.5 |
| 21.0 | 18.2 | 13.0 | 14.3 | 15.4 |
| 21.2 | 20.0 | 13.4 | 15.1 | 16.4 |
| 23.3 | 20.3 | 13.7 | 15.7 | 17.5 |
| 23.7 | 21.8 | 13.9 | 16.1 | 17.8 |
| 24.3 | 22.5 | 14.2 | 16.8 | 18.6 |
| 24.8 | 22.8 | 14.3 | 17.2 | 18.8 |
| 25.6 | 24.9 | 15.1 | 17.2 | 19.3 |
| 26.1 | 25.0 | 15.5 | 17.7 | 19.8 |
| 27.3 | 25.5 | 15.7 | 18.4 | 20.2 |
| 27.9 | 26.2 | 15.9 | 18.8 | 20.3 |
| 29.1 | 26.8 | 16.0 | 19.1 | 20.5 |
| 29.4 | 27.5 | 16.5 | 19.1 | 21.0 |

TABLE 3-continued

X-Ray powder diffractogram of the different crystalline forms
Reflexes [Position °2Th.]

| Mod. I | Mod. II | Mono-DMSO-Solvate | Sesqui-DMSO-Solvate | ¼-Ethylacetate-Solvate |
|---|---|---|---|---|
| 30.5 | 28.1 | 16.8 | 19.6 | 22.8 |
| 31.0 | 28.8 | 17.2 | 20.7 | 23.2 |
| 31.3 | 29.4 | 17.7 | 21.1 | 23.6 |
| 33.2 | 30.0 | 18.4 | 21.4 | 24.0 |
| 34.0 | 30.5 | 18.7 | 21.9 | 24.4 |
| 34.2 | 32.3 | 19.1 | 22.3 | 24.7 |
| 34.9 | 34.0 | 19.6 | 22.6 | 25.1 |
| 36.1 | 34.4 | 20.2 | 22.8 | 25.6 |
| 37.5 | 35.0 | 20.7 | 23.4 | 26.3 |
|  | 35.7 | 21.1 | 23.8 | 26.7 |
|  | 36.5 | 21.4 | 24.6 | 27.1 |
|  |  | 21.8 | 24.9 | 27.4 |
|  |  | 22.2 | 25.4 | 27.6 |
|  |  | 22.4 | 25.6 | 28.2 |
|  |  | 22.6 | 25.9 | 28.6 |
|  |  | 23.0 | 26.7 | 29.1 |
|  |  | 23.5 | 26.8 | 29.7 |
|  |  | 23.9 | 27.3 | 30.0 |
|  |  | 24.3 | 27.9 | 30.7 |
|  |  | 24.6 | 28.4 | 31.3 |
|  |  | 24.8 | 28.8 | 31.8 |
|  |  | 25.6 | 29.4 | 32.7 |
|  |  | 26.0 | 29.6 | 33.1 |
|  |  | 26.3 | 30.5 | 33.5 |
|  |  | 26.7 | 31.5 | 35.2 |
|  |  | 27.2 | 31.7 | 35.9 |
|  |  | 28.8 | 32.1 | 37.6 |
|  |  | 29.3 | 32.5 |  |
|  |  | 29.8 | 33.1 |  |
|  |  | 30.5 | 34.0 |  |
|  |  | 30.8 | 35.0 |  |
|  |  | 31.4 | 35.9 |  |
|  |  | 32.0 | 37.2 |  |
|  |  | 32.3 |  |  |
|  |  | 34.0 |  |  |
|  |  | 34.9 |  |  |
|  |  | 35.7 |  |  |
|  |  | 36.4 |  |  |

TABLE 4

10 Major Reflexes of X-Ray powder diffractogram of the different
crystalline forms
10 Major Reflexes [Position °2Th.]

| Mod. I | Mod. II | Mono-DMSO-Solvate | Sesqui-DMSO-Solvate | ¼-Ethylacetate-Solvate |
|---|---|---|---|---|
| 6.7 | 11.2 | 9.0 | 8.3 | 6.7 |
| 9.1 | 12.6 | 10.8 | 8.4 | 8.3 |
| 14.3 | 12.7 | 11.1 | 13.7 | 8.7 |
| 14.4 | 13.9 | 11.2 | 13.9 | 12.9 |
| 17.8 | 15.2 | 13.0 | 15.7 | 14.2 |
| 19.8 | 17.3 | 15.5 | 17.2 | 17.8 |
| 20.2 | 22.5 | 15.9 | 18.4 | 19.3 |
| 24.8 | 22.8 | 16.0 | 19.6 | 24.0 |
| 25.6 | 25.0 | 20.7 | 21.4 | 25.1 |
| 27.3 | 25.5 | 25.6 | 24.9 | 26.7 |

What is claimed is:

1. A compound of the formula (I)

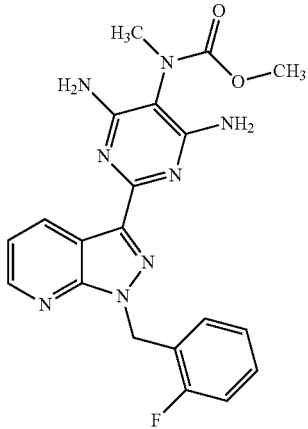

in crystalline form having an X-Ray powder diffractogram comprising at least three peak maxima of the 2 Theta angle selected from 6.7, 9.1, 14.3, 14.4, 17.8, 19.8, 20.2, 24.8, 25.6 and 27.3.

2. The compound of claim 1, wherein the X-ray powder diffractogram comprises peak maxima of the 2 Theta angle of 6.7, 9.1, 14.4, 17.8, and 25.6.

3. The compound of claim 1, wherein the X-Ray powder diffractogram comprises peak maxima of the 2 Theta angle of 6.7, 9.1, 14.3, 14.4, 17.8, 19.8, 20.2, 24.8, 25.6 and 27.3.

4. The compound of claim 1, wherein the ten major reflexes of the X-ray powder diffractogram have peak maxima of the 2 Theta angle of 6.7, 9.1, 14.3, 14.4, 17.8, 19.8, 20.2, 24.8, 25.6 and 27.3.

5. The compound of claim 1, wherein the X-ray powder diffractogram is recorded using Cu K alpha 1 radiation having a wavelength of 1.5406 Å.

6. The compound of claim 2, wherein the X-ray powder diffractogram is recorded using Cu K alpha 1 radiation having a wavelength of 1.5406 Å.

7. A pharmaceutical composition comprising the compound of claim 1 and a pharmaceutically acceptable carrier.

8. A pharmaceutical composition comprising a compound of the formula (I)

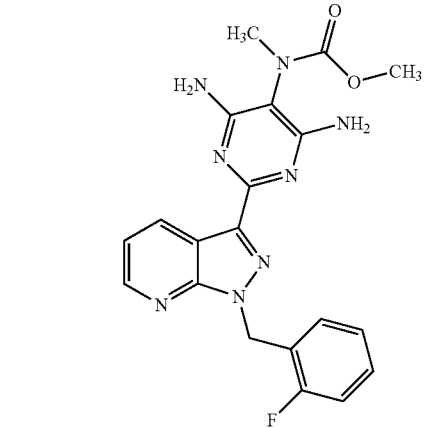

and a pharmaceutically acceptable carrier, in which more than 90 percent by weight relative to the total weight of all forms of the compound of formula (I) in the composition is in crystalline form of Modification (I).

9. The pharmaceutical composition of claim 8, wherein the compound of the formula (I) is characterized by an X-Ray powder diffractogram comprising at least three peak maxima of the 2 Theta angle selected from 6.7, 9.1, 14.3, 14.4, 17.8, 19.8, 20.2, 24.8, 25.6 and 27.3.

10. The pharmaceutical composition of claim 9, wherein the X-ray powder diffractogram comprises peak maxima of the 2 Theta angle of 6.7, 9.1 and 17.8.

11. The pharmaceutical composition of claim 9, wherein the X-ray powder diffractogram comprises peak maxima of the 2 Theta angle of 6.7, 9.1, 14.4, 17.8, and 25.6.

12. The pharmaceutical composition of claim 9, wherein the X-ray powder diffractogram comprises peak maxima of the 2 Theta angle of 6.7, 9.1, 14.3, 14.4, 17.8, 19.8, 20.2, 24.8, 25.6 and 27.3.

13. The pharmaceutical composition of claim 8, in which more than 95 percent by weight relative to the total weight of all forms of the compound of formula (I) in the composition is in crystalline form of Modification (I).

14. A method for the treatment of pulmonary arterial hypertension comprising administering a therapeutically effective amount of the compound of claim 1 to a patient in need thereof.

15. A method for the treatment of pulmonary hypertension associated with thromboembolism (CTEPH) comprising administering a therapeutically effective amount of the compound of claim 1 to a patient in need thereof.

16. A method for the treatment of pulmonary arterial hypertension comprising administering a therapeutically effective amount of a compound of the formula (I)

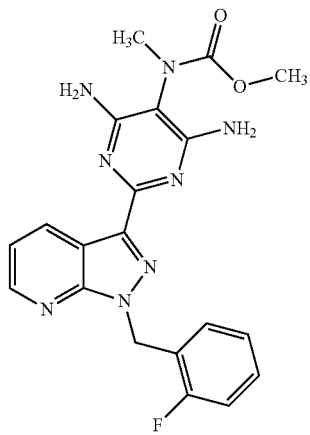

in the crystalline form of Modification I to a patient in need thereof.

17. The method of claim 16, wherein the compound of the formula (I) has an X-Ray powder diffractogram comprising peak maxima of the 2 Theta angle of 6.7, 9.1 and 17.8.

18. The method of claim 16 comprising administering the compound of formula (I) in the crystalline form of Modification I and an endothelin antagonist to the patient in need thereof.

19. The method of claim 16, wherein the compound of the formula (I) has an X-Ray powder diffractogram comprising peak maxima of the 2 Theta angle of 6.7, 9.1, 14.3, 14.4, 17.8, 19.8, 20.2, 24.8, 25.6 and 27.3.

20. A method for the treatment of pulmonary hypertension associated with thromboembolism (CTEPH) comprising administering a therapeutically effective amount of a compound of the formula (I)

in the crystalline form of Modification I to a patient in need thereof.

21. The method of claim 20, wherein the compound of the formula (I) has an X-Ray powder diffractogram comprising peak maxima of the 2 Theta angle of 6.7, 9.1 and 17.8.

22. The method of claim 20, wherein the compound of formula (I) has an X-Ray powder diffractogram comprising peak maxima of the 2 Theta angle of 6.7, 9.1, 14.3, 14.4, 17.8, 19.8, 20.2, 24.8, 25.6 and 27.3.

* * * * *